US008623600B2

(12) United States Patent
Modrich et al.

(10) Patent No.: US 8,623,600 B2
(45) Date of Patent: Jan. 7, 2014

(54) METHODS AND COMPOSITIONS FOR IDENTIFYING INHIBITORS OF MUTSα OR MUTSβ INTERACTION WITH MUTLα

(75) Inventors: Paul L. Modrich, Chapel Hill, NC (US); Ravi R. Iyer, Durham, NC (US); Anna Pluciennik, Durham, NC (US); Miaw-Sheue Tsai, Emeryville, CA (US)

(73) Assignees: Duke University, Durham, NC (US); The United States of America, as Represented by the Secretary of Energy, Washington, DC (US)

( * ) Notice: Subject to any disclaimer, the term of this patent is extended or adjusted under 35 U.S.C. 154(b) by 82 days.

(21) Appl. No.: 13/025,897

(22) Filed: Feb. 11, 2011

(65) Prior Publication Data

US 2011/0195849 A1 Aug. 11, 2011

Related U.S. Application Data

(60) Provisional application No. 61/303,465, filed on Feb. 11, 2010.

(51) Int. Cl.
*C12Q 1/68* (2006.01)
*C07H 21/04* (2006.01)

(52) U.S. Cl.
USPC .......................................... 435/6.1; 536/24.5

(58) Field of Classification Search
None
See application file for complete search history.

(56) References Cited

PUBLICATIONS

Clark et al (The Journal of Biological Chemistry, 2000. vol. 275, No. 47, pp. 36498-36501).*
Habraken et al (Current Biology, 1997. vol. 7, pp. 790-793).*
Spampinato et al (The Journal of Biological Chemistry, 2000. vol. 275, No. 13, pp. 9863-9869).*
Marra et al (PNAS, 1998. vol. 95, pp. 8568-8573).*
Foiry et al (Human Genetics, 2006. vol. 119, pp. 520-526).*
Thomas et al. Methods: vol. 7, pp. 187-197. 1995.*
Brouwer, J. R. et al., "Microsatellite repeat instability and neurological disease," (2009) *Bioessays* 31, 71-83.
Charbonneau, N. et al., "Evidence that hMLH3 functions primarily in meiosis and in hMSH2-hMSH3 mismatch repair," (2009) *Cancer Biol. Ther.* 8, 1411-1420.
Constantin. N, et al., "Human mismatch repair: Reconstitution of a nick-directed bidirectional reaction," (2005) *J. Biol. Chem.* 280, 39752-39761.
Dherin, C. et al, "Characterization of a highly conserved binding site of Mlh1 required for exonuclease I-dependent mismatch repair," (2009) *Mol. Cell Biol.* 29, 907-918.
Drummond, J. T. et al., DHFR/MSH3 amplification in methotrexate-resistant cells alters the hMutSαhMutSβ ratio and reduces the efficiency of base-base mismatch repair, (1997) *Proc. Natl. Acad. Sci, U. S. A.* 94, 10144-10149.
Dzantiev, L. et al., "A defined human system that supports bidirectional mismatch-provoked excision," (2004) *Mol Cell* 15, 31-41.
Edelmann W. et al., "The DNA mismatch repair genes Msh3 and Msh6 cooperate in intestinal tumor suppression," (2000) *Cancer Res*, 60:803-807.
Flores-Rozas et al., "Cdk-interacting protein 1 directly binds with proliferating cell nuclear antigen and inhibits DNA replication catalyzed by the DNA polymerase δ holoenzyme," (1994) *Proc. Natl. Acad. U. S. A.* 91, 8655-8659.
Galio, L. et al., "ATP hydrolysis-dependent formation of a dynamic ternary nucleoprotein complex with MutS and MutL," (1999) *Nucleic Acids Res.* 27, 2325-2331.
Genschel, J. et al., "Isolation of MutSβ from human cells and comparison of the mismatch repair specificities of MutSβ and MutSα," (1998) *J. Biol. Chem.* 273, 19895-19901.
Genschel, J. et al., "Mechanism of 5'-directed excision in human mismatch repair," (2003) *Mol. Cell* 12, 1077-1086.
Gomes-Pereira M. et al., "Pms2 is a genetic enhancer of trinucleotide CAG,CTG repeat somatic mosaicism: Implications for the mechanism of triplet repeat expansion," (2004) *Hum. Mol. Genet.* 13:1815-1825.
Grilley, M. et al., "Isolation and characterization of the *Escherichia coli mutL* gene product," (1989) *J Biol Chem* 264, 1000-1004.
Gu, L. et al., "ATP-dependent interaction of human mismatch repair proteins and dual role of PCNA in mismatch repair," (1998) *Nucleic Acids Res.* 26, 1173-1178.
Habraken, Y. et al., "ATP-dependent assembly of a ternary complex consisting of a DNA mismatch and the yeast MSH2-MSH6 and MLH1-PMS1 protein complexes," (1998) *J. Biol. Chem.* 273, 9837-9841.
Hsieh, P. et al., "DNA mismatch repair: Molecular mechanism, cancer, and ageing," (2008) *Mech. Aging Dev.* 129, 391-407.
Iyer, R. R. et al., "DNA mismatch repair: Functions and mechanisms," (2006) *Chem. Rev*, 106, 302-323.
Iyer, R. R. et al., "The MutSα-proliferating cell nuclear antigen interaction in human DNA mismatch repair," (2008) *J. Biol. Chem.* 283, 13310-13319.
Iyer R. R. et al., "MutLalpha and proliferating cell nuclear antigen share binding sites on MutSbeta," (2010) *J. Biol. Chem.* 285:11730-11739, PMC 2857047.
Johnson, R. E. et al., "Evidence for involvement of yeast proliferating cell nuclear antigen in DNA mismatch repair," (1996) *J. Biol. Chem.* 271, 27987-27990.
Kadyrov, F. A. et al., "Endonucleolytic function of MutLα in human mismatch repair," (2006) *Cell* 126, 297-308.
Kleczkowska, H. E. et al., "hMSH3 and hMSH6 interact with PCNA and colocalize with it to replication foci," (2001) *Genes Dev.* 15, 724-736.
Kolodner, R. D. et al., "Eukaryotic DNA mismatch repair," (1999) *Curr. Opin. Genet. Dev.* 9, 89-96.
Kontopidis, G. et al., "Structural and biochemical studies of human proliferating cell nuclear antigen complexes provide a rationale for cyclin association and inhibitor design," (2005) *Proc. Natl. Acad. Sci. U. S. A.* 102, 1871-1876.

(Continued)

*Primary Examiner* — Celine Qian
(74) *Attorney, Agent, or Firm* — Andrus, Sceales, Starke & Sawall, LLP

(57) ABSTRACT

Disclosed are methods and kits for screening potential inhibitors of MutSβ by screening agents for the ability to selectively inhibit interaction between MutSβ and MutLα. Also disclosed are kits for performing the methods of the invention.

9 Claims, 7 Drawing Sheets

(56) References Cited

PUBLICATIONS

Kratky, O., "X-ray small angle with substances of interest in diluted scattering biological solutions," (1963) *Prog. Biophys. Biophys. Chem*, 13, 105-173.

Kunkel, T. A. et al., "DNA mismatch repair," (2005) *Annu. Rev. Biochem.* 74, 681-710.

Li, G. M., "Mechanism and functions of DNA mismatch repair," (2008) *Cell Res*, 18, 85-98.

Manley K. et al., "Msh2 deficiency prevents in vivo somatic instability of the CAG repeat in Huntington disease transgenic mice," (1999) *Nat. Genet.* 23:471-473.

Mendillo, M. L. et al., "A conserved MutS homolog connector domain interface interacts with MutL homologs," (2009) *Proc. Natl. Acad. Sci. U. S. A.* 106, 22223-22228.

Peltomaki, P., "Role of DNA mismatch repair defects in the pathogenesis of human cancer," (2003) *J. Clin. Oncol.* 21, 1174-1179.

Savouret C. et al., "CTG repeat instability and size variation timing in DNA repair-deficient mice," (2003) *EMBO J.*22:2264-2273, PMC 156074.

Svergun, D. I., "Determination of the regularization parameter in indirect-transform methods using perceptual criteria," (1992) *J. Appl Cryst.* 25, 495-503.

Svergun, D. I. et al., "Determination of domain structure of proteins from X-Ray solution scattering," (2001) *Biophysical journal* 80, 2946-2953.

van den Broek W.J. et al., "Somatic expansion behaviour of the (CTG)n repeat in myotonic dystrophy knock-in mice differentially affected by Msh3 and Msh6 mismatch-repair proteins," (2002) *Hum. Mol. Genet.* 11:191-198.

Wheeler V.C. et al., "Mismatch repair gene Msh2 modifies the timing of early disease in Hdh(Q111) striatum," (2003) *Hum. Mol. Genet.* 12:273-281.

Wright D.J. et al., "The negative charge of Glu-111 is required to activate the cleavage center of EcoRI endonuclease," (1989) *J. Biol. Chem*, 264:11816-11821.

Zhang, N. et al., "hMutSβ is required for the recognition and uncoupling of psoralen interstrand cross-links in vitro," (2002) *Mol. Cell. Biol.* 22, 2388-2397.

Zhang, Y. et al., "Reconstitution of 5'-directed human mismatch repair in a purified system," (2005) *Cell* 122, 693-705.

\* cited by examiner

SEQUENCE LISTING

<160> NUMBER OF SEQ ID NOS: 10

<210> SEQ ID NO 1
<211> LENGTH: 5
<212> TYPE: PRT
<213> ORGANISM: Artificial Sequence
<220> FEATURE:
<223> OTHER INFORMATION: Synthetic peptide - MutLa interaction motif in
      human Exo1 and BLM helicase
<220> FEATURE:
<221> NAME/KEY: misc_feature
<222> LOCATION: (3)..(3)
<223> OTHER INFORMATION: Xaa is Lys or Arg
<220> FEATURE:
<221> NAME/KEY: misc_feature
<222> LOCATION: (4)..(4)
<223> OTHER INFORMATION: Xaa is Tyr or Phe

<400> SEQUENCE: 1

Arg Ser Xaa Xaa Phe
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic peptide

<400> SEQUENCE: 2

Leu Ser Arg Phe Phe
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic peptide

<400> SEQUENCE: 3

Gln Ala Val Leu Ser Arg Phe Phe
1               5

<210> SEQ ID NO 4
<211> LENGTH: 21
<212> TYPE: DNA
<213> ORGANISM: Artificial Sequence
<220> FEATURE:
<223> OTHER INFORMATION: Synthetic DNA

<400> SEQUENCE: 4
ccgctacact tgccagcgcc a                                           21

<210> SEQ ID NO 5
<211> LENGTH: 20
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<223> OTHER INFORMATION: Biotin on 5' end

<400> SEQUENCE: 5
gttcaaaaaa ccccagctcc                                             20

```
<210> SEQ ID NO 6
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa is Leu or Ile
<220> FEATURE:
<221> NAME/KEY: misc_feature
<222> LOCATION: (5)..(6)
<223> OTHER INFORMATION: Xaa can be any naturally occurring amino acid

<400> SEQUENCE: 6

Gln Xaa Xaa Xaa Xaa Xaa Phe Phe
1               5

<210> SEQ ID NO 7
<211> LENGTH: 12
<212> TYPE: PRT
<213> ORGANISM: Artificial Sequence
<220> FEATURE:
<223> OTHER INFORMATION: Synthetic peptide

<400> SEQUENCE: 7

Phe Leu Asn Cys Cys Pro Gly Cys Cys Met Glu Pro
1               5                   10

<210> SEQ ID NO 8
<211> LENGTH: 33
<212> TYPE: PRT
<213> ORGANISM: Artificial Sequence
<220> FEATURE:
<223> OTHER INFORMATION: Synthetic peptide: MSH3

<400> SEQUENCE: 8

Met Ser Arg Arg Lys Pro Ala Ser Gly Gly Leu Ala Ala Ser Ser Ser
1               5                   10                  15

Ala Pro Ala Arg Gln Ala Val Leu Ser Arg Phe Phe Gln Ser Thr Gly
            20                  25                  30

Ser

<210> SEQ ID NO 9
<211> LENGTH: 6
<212> TYPE: PRT
<213> ORGANISM: Artificial Sequence
<220> FEATURE:
<223> OTHER INFORMATION: Synthetic peptide: MSH3delta28

<400> SEQUENCE: 9

Met Gln Ser Thr Gly Ser
1               5

<210> SEQ ID NO 10
<211> LENGTH: 33
<212> TYPE: PRT
<213> ORGANISM: Artificial Sequence
<220> FEATURE:
<223> OTHER INFORMATION: Synthetic peptide: MSH3-F27A-F28A
```

```
-continued

<400> SEQUENCE: 10

Met Ser Arg Arg Lys Pro Ala Ser Gly Gly Leu Ala Ala Ser Ser Ser
1               5                   10                  15

Ala Pro Ala Arg Gln Ala Val Leu Ser Arg Ala Ala Gln Ser Thr Gly
            20                  25                  30

Ser
```

METHODS AND COMPOSITIONS FOR IDENTIFYING INHIBITORS OF MUTSα OR MUTSβ INTERACTION WITH MUTLα

CROSS-REFERENCE TO RELATED APPLICATIONS

This patent application claims the benefit of priority of U.S. Provisional Patent Application No. 61/303,465, filed Feb. 11, 2010, which is incorporated herein by reference in its entirety.

STATEMENT REGARDING FEDERALLY SPONSORED RESEARCH

This invention was partially supported with United States government support awarded by the National Institutes of Health grant numbers R01 GM45190 and P01 CA92584. The United States has certain rights in this invention.

SEQUENCE LISTING

This application includes a Sequence Listing.

INTRODUCTION

The mammalian mismatch repair system stabilizes the genome by correcting DNA biosynthetic errors, preventing illegitimate recombination events, and participating in the cellular response to certain types of DNA damage (reviewed in (1-5)). Mismatch repair deficiency is the cause of hereditary non-polyposis colorectal cancer, and may also be involved in the development of a subset of sporadic tumors (6).

The human mismatch recognition activities MutSα (MSH2-MSH6) and MutSβ (MSH2-MSH3) differ in their substrate specificities: MutSα recognizes base-base mismatches and some insertion-deletion (I/D) mismatches, whereas MutSβ predominantly processes I/D substrates (1-5). MutSα is also capable of recognizing certain types of DNA damage and participates in the checkpoint response to such lesions (7), while MutSβ may cooperate with the nucleotide excision repair machinery in the repair of interstrand cross-links (8, 9). Thus, there is substantial overlap between substrates recognized and processed by these two activities, but the determinants that govern whether a particular lesion is processed by MutSα or MutSβ are not known.

Although MutSα and MutSβ are generally regarded as genetic stabilization activities, both heterodimers have been implicated in the production of certain mutations. MutSα participates in the somatic hypermutation phase of immunoglobulin gene affinity maturation (10), and MutSβ is required for the triplet repeat expansions that are responsible for a number of neurodegenerative diseases (11).

Heteroduplex repair reactions initiated by MutSα and MutSβ have been reconstituted in purified systems that also contain MutLα (MLH1-PMS2), exonuclease 1 (Exo1), RPA, PCNA, RFC, and DNA polymerase δ (12-16). Initiation of repair in the MutSα-dependent system involves activation of a latent endonuclease of MutLα in a reaction that requires a mismatch, MutSα, RFC, PCNA and ATP (16). Action of the MutLα endonuclease is directed to the heteroduplex strand that contains a pre-existing break and is biased to the distal side of the mismatch to yield a molecule in which the mismatch is bracketed by strand breaks. This multiply incised intermediate serves as substrate for Exo1, which is activated by MutSα in a mismatch-dependent manner, leading to mismatch removal. The ensuing gap is filled by RPA and repaired by DNA polymerase δ in a reaction that also depends on PCNA and RFC. Although a MutSβ-dependent repair reaction directed by a 5'-strand break has been reconstituted from purified components (15), it is not known whether activation of the MutLα endonuclease occurs in a MutSβ-dependent manner. Coordination of these activities during the course of repair is presumably mediated by a temporally evolving set of protein-protein and protein-DNA interactions. The most thoroughly studied of the multi-protein assemblies involved in mismatch repair have been the MutSα-MutLα complex that assembles on heteroduplex DNA (17-19) and the MutSα-PCNA complex that has been observed both in solution and on DNA (20, 21). While the former complex is generally believed to play an important role in the reaction (22), disruption of the MutSα-PCNA interaction confers only a partial mismatch repair defect in vivo and in vitro (20, 21, 23). Although the MutSβ-PCNA and MutSβ-MutLα complexes have been the subject of only limited study (23-26), yeast strains carrying mutations in the PCNA-binding motif of MSH3 display hypermutability similar to that of MSH3 null (23). Also, little is known regarding the functional significance of the MutSβ-MutLα interaction. We demonstrate here that MutSβ differs from MutSα in the manner that it interacts with PCNA and MutLα.

SUMMARY

In one aspect, the invention includes methods for testing an agent for the ability to inhibit MutSβ, by forming an assay that includes the agent, MutLα and MutSβ, and evaluating interaction between MutLα and MutSβ in the assay. The methods may also involve testing the agent for the ability to inhibit the interaction between MutLα and MutSα by forming an assay including the agent, MutLα and MutSα, and evaluating interaction between MutLα and MutSα in the assay. The methods may be conducted in the presence or absence of suitable heteroduplex DNA substrate.

These methods will allow the identification of agents having the ability to specifically inhibit the interaction between MutLα and MutSβ. Identification of these agents may be used to develop structurally related agents that can then be tested by the methods of the invention for the ability to specifically inhibit the interaction between MutLα and MutSβ. It is envisioned that agents having the ability to specifically inhibit the interaction between MutLα and MutSβ could be useful in treating individuals having or at risk for developing deleterious conditions associated with MutSβ activity, e.g., neurological disorders caused by the expansion of $(CAG)_n$ repeats.

The methods of the invention will also allow the identification of agents having the ability to specifically inhibit the interaction between MutLα, and MutSα. Such agents may be useful as research tools in further studies of interactions of proteins involved in mismatch repair.

In another aspect, the invention provides a kit for screening agents for the ability to inhibit the interaction between MutLα and MutSα or MutSβ that includes MutLα, MutSα and/or MutSβ, and a linear heteroduplex DNA substrate or a linear homoduplex DNA control attached to a solid support through one end of the substrate or control. Suitable DNA substrates contain a MutSα- or MutSβ-recognizable mismatch.

BRIEF DESCRIPTION OF THE DRAWINGS

FIG. 7A is a plot of scattering intensities (I) versus the scattering vector Q are shown for MutSβ, MutSβΔ28, an equimolar mixture of MutSβ and PCNA, and PCNA alone (reproduced from (21)). Guinier plots (ln I vs. $Q^2$) (32), linear portions of which are shown (inset), were derived from scattering profiles and were used to determine radii of gyration (Table 1).

FIG. 7B is a plot of forward scattering intensities I(0) (intensity at θ=0°) for MutSβ (filled triangle), MutSβΔ28 (open triangle) and an equimolar mixture of MutSβ and PCNA (filled square) derived from concentration-normalized scattering data by the Guinier approximation (32) as a function of the molecular mass of each molecule (41). Data are plotted alongside results reproduced from Iyer et al. (21) for (a) PCNA, (b) MutSαΔ341, (c) MutSαΔ12, (d) MutSα, (e) MutSα-PCNA.

FIG. 7C Apparent Rg as a function of protein concentration is shown for MutSβ (filled triangles), MutSβΔ28 (open triangles), and the MutSα-PCNA complex (filled squares). Data for PCNA (filled circles) are reproduced from Iyer et al. (21).

FIG. 7D P(r) plots from FIG. 5A, excluding that for PCNA, are reproduced alongside pairwise interatomic distances calculated from the crystal structures of MutSαΔ341·DNA (40) and *E. coli* MutS·DNA (39).

DETAILED DESCRIPTION

Figure 1:
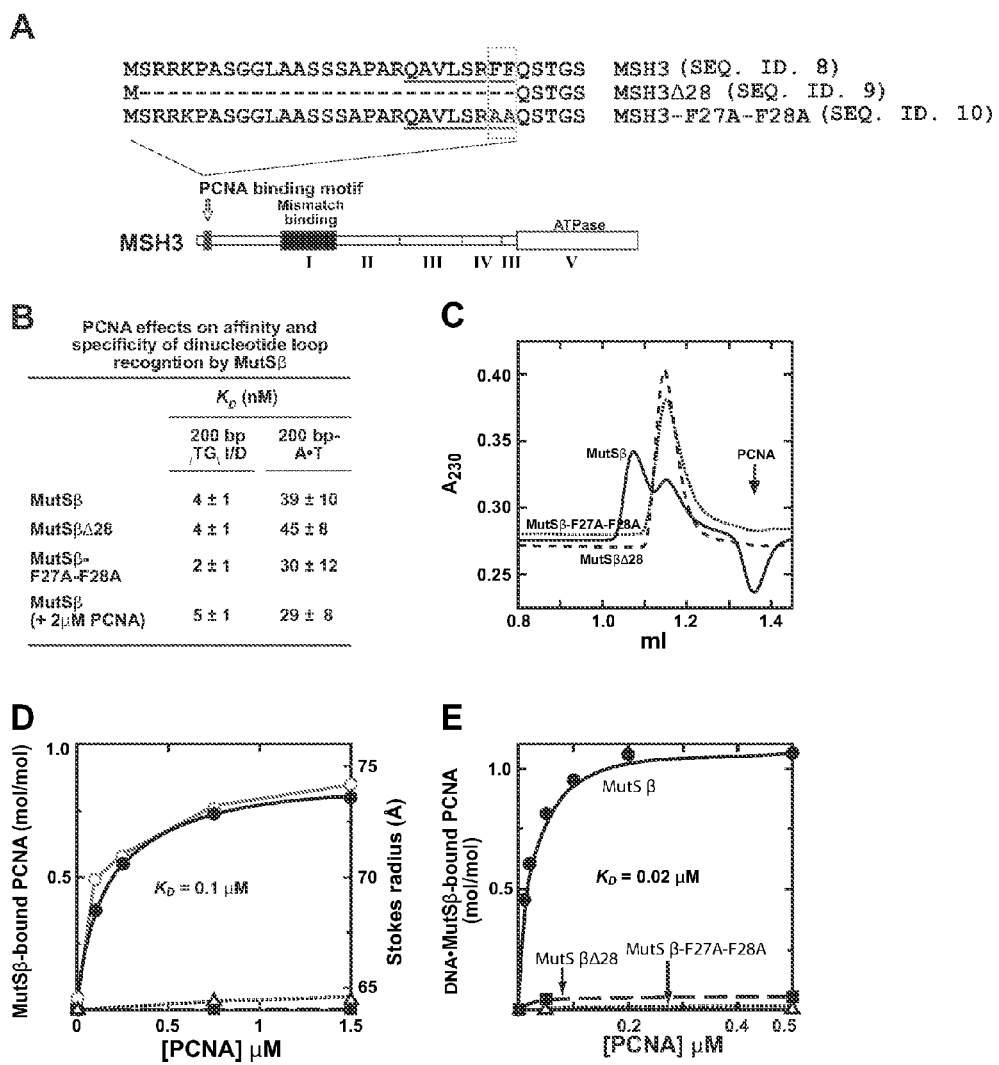
FIG. 1A includes an alignment of the N-terminal regions of MutSβ MSH3 variants and a schematic representation of domains within MSH3, as predicted by sequence alignment of MSH3 with MSH6.
FIG. 1B compares the binding affinities of MutSβ variants for an insertion/deletion (I/D) DNA heteroduplex or control homoduplex, in the presence and absence of PCNA.
FIG. 1C shows the elution profile of complexes of PCNA with MutSβ and MutSβ variants (MutSβ (solid line), MutSβΔ28 (dotted line), and MutSβ-F27A-F28A (dashed line)) following Hummel-Dreyer equilibrium gel filtration.
FIG. 1D shows extent of binding of PCNA to MutSβ (closed circles), MutSβΔ28 (closed squares), or MutSβ-F27A-F28A (open triangles) as a function of PCNA concentration.
FIG. 1E shows the binding PCNA to MutSβ variants as a function of PCNA concentration.

MutSα (MSHS2-MSH6) and MutSβ (MSH2-MSH3) are the primary DNA mismatch recognition factors in humans. Whereas MutSα recognizes and processes base-base mismatches and some insertion-deletion loops, MutSβ predominantly recognizes insertion-deletion loops. These proteins are required for the maintenance of genome integrity. Surprisingly, MutSβ has been implicated in the somatic and intergenerational expansion of (CAG)$_n$ repeats that cause hereditary neurological diseases such as myotonic dystrophy, Huntington's disease, Kennedy's disease, and several types of spinocerebellar ataxia.

In light of the foregoing, it is envisioned that inhibitors of MutSβ may suppress (CAG)$_n$ somatic expansion in affected individuals in order to delay the onset of or ameliorate neurodegenerative symptoms. However, a major obstacle to developing therapies that inhibit MutSβ is that, because MutSα and MutSβ share significant homology, inhibitors of MutSβ are likely to also affect MutSα Inhibition of MutSα function would be undesirable, because MutSα inactivation confers strong cancer predisposition. In contrast, MutSβ inactivation in mice confers a relatively mild phenotype Inhibitors that selectively inhibit MutSβ have yet to be identified.

Both MutSα and MutSβ activate a latent endonuclease in MutLα (MLH1-PMS2) in a reaction that requires the sliding clamp PCNA, the RFC clamp loader, and a mispaired DNA substrate. The interaction between MutSα/β and MutLα is considered to be essential for mismatch repair function. However, as described in the Examples below, we have discovered that the mechanisms of MutSα- and MutSβ-mediated mismatch repair are substantially different. In particular, these proteins differ in their modes of interaction with PCNA and MutLα. Whereas MutSα can simultaneously associate with PCNA and MutLα because PCNA and MutLα bind independently to MutSα, PCNA competes with MutLα for binding to MutSβ due to overlap in binding sites on the MSH3 subunit of MutSβ for PCNA and MutLα. MSH3 PIP box mutations abolish MutSβ interaction with both PCNA and MutLα, whereas PIP box mutations in MutSα do not interfere with MutSα-MutLα interaction. Thus, it may be possible to identify small molecule inhibitors that interfere with MutSβ-MutLα interaction but do not substantially interfere with MutSα-MutLα interaction, i.e., inhibitors that selectively target MutSβ-MutLα interaction.

Our discovery of differences in the mode of interaction of MutSα and MutSβ with MutLα will facilitate the identification of selective inhibitors of the MutSβ-MutLα interaction. We intend to screen for specific inhibitors of MutSβ function by identifying molecules that specifically inhibit MutSβ-MutLα interaction. We envisage that such inhibitors may fall into three types of inhibitors. One type of inhibitor would include molecules that bind MSH2 or MSH3, in regions removed from the MutSβ-MutLα interaction site, that affects MutSβ-MutLα interaction by allosteric effects. A second type of inhibitor could bind residues of MutSβ and/or MutLα in the vicinity of the interaction interface responsible for MutSβ-MutLα interaction. A third type of inhibitor may bind to MLH1 or PMS2 in a manner that specifically attenuates MutSβ-MutLα interaction without substantially attenuating MutSα-MutLα interaction.

Additionally, it is envisaged that screening for inhibitors having differential effects on MutSα/β interactions with MutLα will identify molecules that selectively interfere with MutSα-MutLα interaction but not MutSβ-MutLα interaction. Such inhibitors may be used as laboratory reagents to study MutSα and MutSβ function in various DNA metabolic processes.

The Examples below describe suitable assays that may be performed in accordance with the method of the invention. However, it is envisioned that any method of screening an agent for its effect on MutSβ-MutLα interaction and MutSα-MutLα interaction could be used in the methods of the invention, and would fall within the scope of the invention.

As described in the Examples below, MutSβ-MutLα interaction and MutSα-MutLα interaction may be assessed in the presence of a suitable heteroduplex DNA substrate. The DNA substrates for use in the methods and kits of the invention may be attached at one end to a solid support, such as a polystyrene microtiter plate. As one of ordinary skill in the art will appreciate, any suitable solid support of any suitable material may be used.

In the Examples, it is proposed that the DNA substrate may be attached to a solid support either through interaction between a fluorescein label at one end with an anti-fluorescein antibody coating the solid support, or between a biotin tag at one end and streptavidin coating the solid support. However, it is envisaged that the DNA substrate may be attached using any chemistry suitable for attaching DNA to a solid support Suitable DNA substrates include those that comprise a MutSβ- or MutSα-recognizable mismatch. A MutSβ-recognizable mismatch includes an appropriate insertion/deletion mismatch. A MutSα-recognizable mismatch includes an appropriate base-base or insertion/deletion mismatch. The DNA substrates described in the Examples were approximately 200 bp long. However, DNA substrates of any suitable length may be used. Preferably, the DNA substrate is sufficiently long to allow formation of a ternary complex between the DNA, MutLα and MutSα or MutSβ.

In order to maintain the ternary complex to enhance detection, the free end of the DNA substrate, i.e, the end that is not attached to the solid support, may optionally be modified to include bound protein that promotes trapping of the MutSβ-MutLα or MutSα-MutLα complex on the DNA. For example, the free end could be modified to include biotin that is in turn bound by monovalent avidin. Alternatively, the free end could be modified to include a label such as fluorescein at the free end, to which anti-fluorescein antibody may be bound. In yet another embodiment, the end may be modified to include an EcoRI site near the free terminus and a hydrolytically dead mutant of EcoRI endonuclease can be used to bind to the EcoRI site. It is envisioned that other proteins may be used to stabilize the ternary complex by binding at or near the free end of the DNA substrate.

Any suitable method of detection may be used to detect MutSβ-MutLα interaction and MutSα-MutLα interaction, including immunological or FRET-based methods.

The Examples also describe the direct detection of MutSβ-MutLα interaction or MutSα-MutLα interaction, i.e., interaction that occurs in the absence of DNA. It is envisioned that these and any other suitable method of detecting direct MutSβ-MutLα interaction or MutSα-MutLα interaction may be used to assay agents for the ability to affect MutSβ-MutLα interaction or MutSα-MutLα interaction.

While the methods of the invention are most conveniently performed in a high-throughput format, the present invention is intended to encompass single assays as well.

The methods and kits of the invention can be used to screen any suitable agent for its ability to affect MutSβ-MutLα interaction or MutSα-MutLα interaction. Suitable agents may include, for example, libraries of agents, e.g., libraries of small molecules. Suitably, the small molecules have a molecular weight of about 800 Daltons or less, but could also include small peptides with a mass somewhat greater than this value. The agents may be tested individually or initially, in pools of, for example, five or ten agents.

An agent that is an inhibitor of MutSβ-MutLα or MutSα-MutLα interaction is one that reduces interaction relative to the interaction that takes place in the absence of the agent. For an agent to be identified as an inhibitor of MutSβ-MutLα or MutSα-MutLα interaction, it is not necessary that inhibition be 100%. Preferably, interaction is inhibited at least 10%, 20%, 30%, 40%, 50%, 60%, 70%, 80%, 90% or more. An agent that is selective inhibitor of MutSβ-MutLα interaction inhibits MutSβ-MutLα interaction to a greater extent than it inhibits MutSα-MutLα interaction. Preferably, inhibition of MutSβ-MutLα interaction is maximized and inhibition of MutSα-MutLα interaction is minimized. However, an agent that affords less than 100% inhibition of MutSβ-MutLα interaction may still have therapeutic value, or can be modified to afford greater inhibition, while some inhibition of MutSα-MutLα interaction may be acceptable, depending on the severity of the condition being treated. Most preferably, the selective inhibitor of MutSβ-MutLα interaction does not inhibit MutSα-MutLα interaction.

Protein-protein interactions are thought to coordinate the sequence of molecular events involved in DNA mismatch repair. A number of multi-protein assemblies have been documented in this system including MutSα-PCNA, MutSβ-PCNA, MutSα-MutLα, MutSβ-MutLα, MutLα-PCNA, MutSα-ExoI, MutLα-ExoI, and ExoI-PCNA (1-5). Of these, the MutSα-PCNA complex has received the most attention in the literature, but recent studies suggest that this interaction may play only a limited role in the error correction reaction (20, 21, 23).

Because MSH3, like MSH6, interacts with PCNA via a PIP box located near its N-terminus, it might be expected that the MutSβ-PCNA complex may display similar characteristics. However, the Examples below present results that indicate that this is not the case. The affinity of MutSβ for PCNA is ~8-fold higher than that of MutSα, a difference that may be necessitated by the fact that the MutSβ levels in human cells are 5- to 8-fold lower than that of the MSH2-MSH6 heterodimer (30, 44). Furthermore, while the stoichiometry of the MutSα-PCNA complex is limited to 1:1 even when MutSα is in molar excess (21), as much as 20% of the MutSβ-PCNA complexes are multivalent under conditions of MutSβ excess. This valency difference could reflect steric factors in that MutSβ is significantly smaller than MutSα. Despite these differences, complex formation between MutSβ and PCNA does not significantly alter the affinity or specificity of MutSβ for a -TG- insert, a property it shares with MutSα.

However, the most striking difference between MutSβ and MutSα is the finding described here that the modes of interaction of the two mismatch recognition activities with PCNA and MutLα differ dramatically. In contrast to MutSα, which can interact independently with PCNA and MutLα, interaction of these two proteins with MutSβ occurs in an either/or fashion. As discussed above, MSH3 PIP box mutations compromise MutSβ interaction with both PCNA and MutLα. Furthermore, PCNA competes with MutLα for binding to MutSβ and inhibits ATP-dependent assembly of the DNA-MutSβ-MutLα ternary complex, an effect that is reversed by p21, which is known to interact strongly with PCNA (45). The simplest interpretation of these results is that the MutSβ motif(s) involved in its interaction with MutLα partially overlap with the MSH3 PIP box responsible for the MutSβ-PCNA interaction. It is noteworthy in this regard that an R-S-K/R-Y/F-F (SEQ ID NO: 1) sequence has been identified as a MutLα interaction motif in human Exo1 and BLM helicase (46). A similar highly conserved motif L-S-R-F-F (SEQ ID NO: 2) overlaps with the MSH3 PIP box (Q-A-V-L-S-R-F-F) (SEQ ID NO: 3), and may correspond to one component of the MutLα binding site within MutSβ. To our knowledge, this is the first instance where residues within the PCNA-binding motif of a protein are also employed for interaction with a second activity.

Recently, Fishel and colleagues (47) have described an interaction between human MLH1 and a polypeptide corresponding to the N-terminal 250 residues of human MSH3; interaction of MLH1 with MSH2 was not observed in this study. These findings are consistent with those described here. By contrast, studies in *Saccharomyces cerevisiae* (48) have implicated yMSH2 residues in the interaction of yMutSα with yMutLα, although mutational alteration of the yMSH2 residues in question did not result in an interaction defect as severe as that described in our study. It is thus conceivable that MSH2 sequence elements contribute to MutSβ-MutLα interaction, but if this is the case, residues in the vicinity of the MSH3 PIP box must also be required.

Our finding that PCNA and MutLα interact in an either/or fashion with MutSβ may reflect steric interference effects but could also be indicative of use of common interaction interfaces. For example, MutSβ and MutLα interaction with a common PCNA motif would account for our findings, as would MutSβ and PCNA interaction with a common interface on MutLα.

Since ATP-dependent assembly of a ternary complex involving heteroduplex DNA and a MutS and MutL homolog is believed to be a key step in the initiation of mismatch repair (3, 4), the inability of MutSβ PIP box mutants to support MutLα endonuclease activation, mismatch-provoked excision and repair might be attributed to the inability of these mutants to support ternary complex formation. However, it is also possible that in contrast to the MutSα-initiated reaction, MutSβ interaction with PCNA may be a key step in MutSβ-initiated repair events. The pleiotropic nature of these mutants does not permit distinction between these possibilities, although our results almost certainly indicate that MutSα- and MutSβ-initiated mismatch repair events proceed by distinct mechanisms.

Interestingly, *Saccharomyces cerevisiae* studies have suggested that while PIP box integrity may be required for MSH3 function, it has only a limited role in MSH6 activity (20, 23). In an msh3 null background, the rate of frameshift mutagenesis within a $(A)_{14}{:}(T)_{14}$ run was ~30-fold higher for an msh6Δ allele ($1.5 \times 10^{-3}$) than for a msh6 PIP box mutant ($5.2 \times 10^{-5}$) (23). By contrast, deletion of msh3 in an msh6 null background resulted in a mutation rate ($1.5 \times 10^{-3}$) only ~2-3 fold higher than that observed upon inactivation of the MSH3 PIP-box ($6.5 \times 10^{-4}$) (23). Our findings that MSH3 PIP-box mutations are pleiotropic may explain these observations.

A potential mechanistic implication of our findings is that whereas PCNA is required for both MutSα- and MutSβ-dependent activation of MutLα endonuclease, a transient increase in local PCNA concentration could lead to specific destabilization of the MutLα-MutSβ-DNA complex, thus aborting a MutSβ-initiated event to allow a MutSα-dependent reaction to proceed unhindered. Since some I/D mispairs are subject to either MutSα- or MutSβ-dependent repair (30), this type of PCNA-mediated switch might function to control processing of such lesions by a particular pathway.

The following non-limiting examples are intended to be purely illustrative.

EXAMPLES

Experimental Procedures

MutSβ Expressing Baculovirus Constructs—

The baculoviral donor plasmid pFastBacDual-MSH2-MSH3 (9) that harbors full-length MSH2 and MSH3 was modified by PCR mutagenesis to yield pFastBacDual-MSH2-MSH3Δ28 which contains intact MSH2 and an N-terminally truncated MSH3 gene encoding amino acids 29-1137 of full-length MSH3 beginning with N-Met (FIG. 1A). A second construct, pFastBacDual-MSH2-MSH3-F27A-F28A harboring MSH3 that contains Phe to Ala amino acid substitutions at positions 27 and 28 (FIG. 1A), was also prepared by PCR mutagenesis of the full-length construct. High-titer recombinant baculoviruses were prepared from the expression vectors, and used to infect Sf9 cells for protein expression.

DNA Substrates and Proteins—

Bacteriophages f1MR72 and f1MR73 were constructed by oligonucleotide mutagenesis of f1MR23 and f1MR24 (27), respectively, resulting in substitution of an EcoRV site for residues 5501-5506 as described for phages f1MR70 and f1MR71 (28). 6,440 bp dinucleotide insertion/deletion heteroduplex DNAs (-TG-) were constructed as described (27) from phages f1MR72 and f1MR73 and contained a site specific nick in the complementary DNA strand 128 bp 3' or 5' to the mismatch as viewed along the shorter path in the circular molecules. The strand break for 5'-TG- was introduced by cleavage with Sau96I while the strand break in 3'-TG- was introduced by cleavage with EcoRV (28). Substrates for analyses of DNA-protein assemblies by SPRS were 200 bp in length, and were prepared as follows. Primers 5'-CCGCTA-CACTTGCCAGCGCCA-3' (SEQ ID NO: 4) and 5'-biotin-GTTCAAAAAACCCCAGCTCC-3' (SEQ ID NO: 5) were used to generate 200-bp and 202-bp PCR products from f1MR23 and f1MR24 (27), respectively. The strands were separated by denaturing HPLC (29) and reannealed to generate a heteroduplex containing a centrally positioned -TG- loop, or an otherwise identical homoduplex.

MutSβ, MSH2-MSH3Δ28 (MutSβΔ28), and MSH2-MSH3-F27A-F28A (MutSβ-F27A-F28A) were prepared from baculovirus-infected 519 cells by a procedure essentially identical to that described for native human MutSβ (30). All other proteins were purified as described in Iyer et al. (21), and references listed therein. Concentrations of MutSβ are expressed as heterodimer equivalents using an extinction coefficient of 136,690 $M^{-1}$ $cm^{-1}$ at 280 nm for MutSβ and its variants determined as described (31).

Analyses of Protein-Protein and Protein-DNA Assemblies—

Gel filtration chromatography was performed at 4° C. as described (21). SPRS experiments were done on a Biacore-2000 (17,21) in a buffer composed of 25 mM HEPES-NaOH (pH 7.5), 150 mM NaCl (unless otherwise indicated), 5 mM $MgCl_2$, 1 mM EDTA, and 0.1 mM dithiothreitol. Streptavidin sensor chips were derivatized with ~200 response units of a 200 bp -TG- I/D heteroduplex, or an otherwise identical homoduplex DNA, via a 5' biotin tag.

Far-western analyses were performed by spotting 0.25-4 pmol of the indicated proteins on a nitrocellulose membrane (Protran, Whatman) or by electrophoresing 2 pmol protein through a 7% SDS-polyacrylamide gel, followed by transfer to nitrocellulose. After incubation in blocking buffer (10 mM Tris-HCl (pH 8.0), 150 mM NaCl, 1 mM EDTA, 0.1% Triton X-100, and 5% milk solids) for 1 hour at room temperature, the membrane was incubated overnight at 4° C. with PCNA or MutLα in blocking buffer as indicated, followed by two buffer washes. Presence of bound MutLα or PCNA was detected immunochemically with mouse anti-MLH1 or anti-PCNA antibodies.

Small Angle X-ray Scattering (SAXS) experiments— SAXS was performed on the Sibyls beamline 12.3.1 at ALS, Berkeley. Scattering data were collected over a range of protein concentrations (10-50 μM) in a buffer containing 25 mM HEPES-KOH, pH 7.5, 150 mM KCl, 5 mM $MgCl_2$, and 1 mM DTT and data analysis were performed as described (21). For SAXS-based stoichiometry measurements, scattering data were collected for mixtures of PCNA and MutSβ (or MutSβΔ28) in which PCNA concentration was varied (3.3-105 μM) at a fixed concentration of MutSβ (10, 20 or 35 μM) or MutSβΔ28 (10 μM) in the buffer described above. Concentration-normalized scattering data were then used to derive forward scattering intensities I(0) (intensity at θ=0°) (32). The theoretical I(0) for a protein mixture was estimated as the sum of the expected I(0) contributions of each component of that mixture, the latter property being the product of mass fraction of the component and the I(0) value corresponding to its molecular mass. Since protein concentrations were much higher than the $K_d$ for MutSβ-PCNA interaction, the limiting species was assumed to be present only in the $(MutSβ)_n$-PCNA complex.

Mismatch Repair Assays—

Bidirectional mismatch-provoked excision and repair assays were carried out at 37° C. for 30 min by complementation of 100 μg of RL95-2 ($MSH2^{-/-}$) nuclear extracts with recombinant MutSβ as indicated in 10 μl reactions containing 20 mM Tris-HCl (pH 7.6), 110 mM KCl, 5 mM $MgCl_2$, 1 mM reduced glutathione, 1.5 mM adenosine triphosphate, 0.05 mg/mL bovine serum albumin and a 6440-bp -TG- I/D heteroduplex or homoduplex substrate (2.4 nM) (21). Mismatch repair in extracts was performed in a similar manner, except that the reactions also contained 0.1 mM each of dATP, dTTP, dCTP, and dGTP. Excision was scored by conversion of DNA to a NheI-resistant form (33), and repair was measured by restoration of XcmI sensitivity to the heteroduplex DNA (27). MutLα endonuclease assays (16) were carried out in a purified system composed of MutSβ (22 nM), MutLα (50 nM), RFC (15 nM), PCNA (100 nM), and an I/D heteroduplex or homoduplex DNA substrate (1.2 nM) at 37° C. for 10 min in a 20 μl reaction in the buffer described above. Reaction products were resolved on alkaline agarose gels, and extent of MutLα-catalyzed incision measured by indirect end-labeling (16).

Example 1

Characterization of Interaction Between MutSβ and PCNA

MutSβ interacts with PCNA via a conserved QXX(L/I) XXFF motif (SEQ ID NO: 6) that resides near the N-terminus of MSH3 (23, 24, 26), but the molecular nature of the MutSβ-PCNA complex has not been examined. To address the nature of this interaction as well as the functional consequences of its disruption, we constructed MSH3 variants in which the PCNA-binding motif (PIP box) was either deleted (MSHβΔ28) or altered by amino acid substitution mutation (MSH3-F27A-F28A) (FIG. 1A). These variants were co-expressed with MSH2 and purified as stable heterodimers. Both mutant heterodimers display Stokes radii comparable to the wild type protein as determined by gel filtration chromatography (Table I).

Interactions between the MSH3 variants and PCNA were further characterized, and the results are presented in FIG. 1B-1E. DNA affinities of MutSβ, MutSβΔ28, and MutSβ-F27A-F28A were determined by SPRS (Experimental Procedures) by flowing the proteins over a sensor chip derivatized with 200 bp homoduplex or -TG- I/D heteroduplex DNA Mass response units at saturation were recorded as a function of MutSβ concentration and fit to a rectangular hyperbola to yield apparent affinities shown. PCNA effects on MutSβ-DNA interaction were assessed by titration with MutSβ in presence of 2.0 μM PCNA (FIG. 1B).

Interaction of PCNA with MutSβ in the absence of DNA was evaluated by equilibrium gel filtration (Experimental Procedures). Ten-μl samples containing 1 μM MutSβ (or 1.14 μM MutSβΔ28 or 1.0 μM MutSβ-F27A-F28A) and 0.75 μM PCNA were loaded onto a 2.4 ml Superdex 200 column equilibrated with 0.75 μM PCNA and the column was developed isocratically at 0.01 ml/min. Protein elution profiles as detected by absorbance at 230 nm are shown for MutSβ, MutSβΔ28, and MutSβ-F27A-F28A. (FIG. 1C)

With reference to FIG. 1D, extents of PCNA trimer binding to MutSβ (closed circles), MutSβΔ28 (closed squares), or MutSβ-F27A-F28A (open triangles) were determined from trough areas as a function of free PCNA concentration. Binding isotherms shown were determined by nonlinear least squares fit to a rectangular hyperbola, which yielded a $K_d$ of 0.10 μM and a stoichiometry of 0.8-0.9 PCNA homotrimer per wild type MutSβ heterodimer. Formation of the MutSβ-PCNA complex is associated with an increase in apparent Stokes' radius (open circles).

Interaction parameters of PCNA with DNA-bound MutSβ were determined by SPRS (FIG. 1E). Solutions containing 0.10 μM MutSβ (or MutSβΔ28 or MutSβ-F27A-F28A) and 0-0.50 μM PCNA were allowed to flow over a sensor chip derivatized with a 200 bp -TG- I/D heteroduplex. The amount of PCNA bound to the sensor surface was determined as a function of PCNA concentration for MutSβ (circles), MutSβΔ28 (squares), or MutSβ-F27A-F28A (open triangles) by subtracting the mass response units (RU) recorded for each MutSβ variant alone from that determined in the presence of PCNA. Molar stoichiometries were calculated assuming that one RU of MutSβ (232 kDa) corresponds to 0.37 RU for the PCNA trimer (86 kDa). Data were fit to a rectangular hyperbola, yielding an apparent $K_d$ of 0.02 µM, and a stoichiometry of 1 mole of PCNA per mole of MutSβ.

To determine whether these MSH3 mutations altered the mismatch recognition activity of MutSβ, we used surface plasmon resonance spectroscopy (SPRS) to measure affinities of MutSβ, MutSβΔ28 and MutSβ-F27A-F28A for a 200 bp -TG- dinucleotide I/D heteroduplex, or an otherwise identical homoduplex. Apparent affinities and specificities of the heterodimer (FIG. 1C). Although MutSβΔ28 and MutSβ-F27A-F28A efficiently bind heteroduplex DNA (FIG. 1B), PCNA interaction with the heteroduplex-bound mutant proteins was almost undetectable (FIG. 1E). The apparent affinity of PCNA for DNA-bound MutSβ as judged by SPRS is ~5-fold higher than that for free MutSβ as determined by the Hummel-Dreyer method. A similar difference has been observed for affinities of the MutSα-PCNA complex determined by the two methods (21), and is likely due to avidity or re-binding artifacts that are known to occur when multivalent species such as PCNA are present in the mobile phase of SPRS analysis (34).

TABLE 1

Biophysical properties of MutSβ and MutSβ-PCNA derived from SAXS and gel filtration. Radii of gyration ($R_g$) were determined from Guinier plots (FIG. S2A, inset) (32), in which SAXS data collected over a range of protein concentration (FIG. S2C) were extrapolated to zero concentration. The maximum particle dimension ($D_{max}$) was estimated from the P(r) plots (49) shown in FIG. 5A. Stokes' radii were determined by gel filtration (Experimental Procedures). See also FIG. S2.

| Sample | MW kDa | $R_g$ (Å) calculated | SAXS $R_g$ (Å) Guinier | $R_g$ (Å) P[r] | $D_{max}$, (Å) | Gel filtration Stokes' radius (Å) |
|---|---|---|---|---|---|---|
| MutSβ | 232 | — | 52 ± 0.2 | 49 ± 0.1 | 165 | 64 |
| MutSβΔ28 | 229 | — | 50 ± 0.5 | 48 ± 0.1 | 160 | 64 |
| MutSβ-F27A-F28A | 232 | — | — | — | — | 64 |
| PCNA[a] | 86 | 34 | 33 ± 0.1 | 34 ± 0.1 | 92 | 40 |
| MutSβ + PCNA (1:1) | 318 | — | 67 ± 1 | 65 ± 0.2 | 220 | 74 |
| MutSβΔ28 + PCNA (1:1) | — | — | 50 ± 0.4 | — | — | — |

[a]Data for PCNA is reproduced from Iyer et al. (21).

MutSβ variants did not differ significantly from that obtained with the wild type protein (FIG. 1B). Furthermore, wild type and mutant forms of MutSβ dissociated with similar kinetics from heteroduplex DNA upon ATP challenge (not shown). The presence of 2.0 µM PCNA, a saturating concentration for MutSβ-PCNA complex formation (see below), did not significantly alter the affinity or specificity of MutSβ interaction with heteroduplex/homoduplex DNA (FIG. 1B).

The MutSβ-PCNA complex was characterized by the Hummel-Dreyer equilibrium gel filtration procedure that was previously employed to determine equilibrium parameters that govern formation of the MutSα-PCNA complex (21). The Hummel-Dreyer elution profile for MutSβ (FIG. 1C) in the presence of 0.75 µM PCNA shows two distinct but overlapping peaks followed by a trough at ~1.35 ml that represents depletion of PCNA from the running buffer due to complex formation with MutSβ. Because the later eluting peak (1.14 ml) corresponds to free MutSβ, we infer that earlier peak (1.1 ml) represents the MutSβ-PCNA complex. By contrast, MutSβΔ28 and MutSβ-F27A-F28A elute as single peaks (1.14 ml) corresponding to uncomplexed MutSβ. Furthermore, as judged by absence of a significant trough at 1.35 ml, the two mutant heterodimers fail to deplete PCNA from the equilibrating buffer, indicating that their ability to bind PCNA has been severely compromised. The extent of PCNA binding to MutSβ was a hyperbolic function of PCNA concentration corresponding to an apparent $K_d$ of 0.10 µM and a stoichiometry of 0.8-0.9 PCNA trimer per MutSβ heterodimer (FIG. 1D). Formation of complex with PCNA increases the Stokes radius of MutSβ from 64 Å to 74 Å (Table I).

PCNA binding to DNA-bound MutSβ was evaluated by SPRS. As determined by this procedure DNA-bound MutSβ interacts with PCNA with an apparent $K_d$ of 0.020 µM and a stoichiometry of 1.1 mol of PCNA trimer per mol of MutSβ

Example 2

Characterization of Interaction of MutSβ or MutSα PIP Box Mutants with MutLα

MutSβ PIP Box Mutants are Defective in MutLα Interaction—

Figure 2:
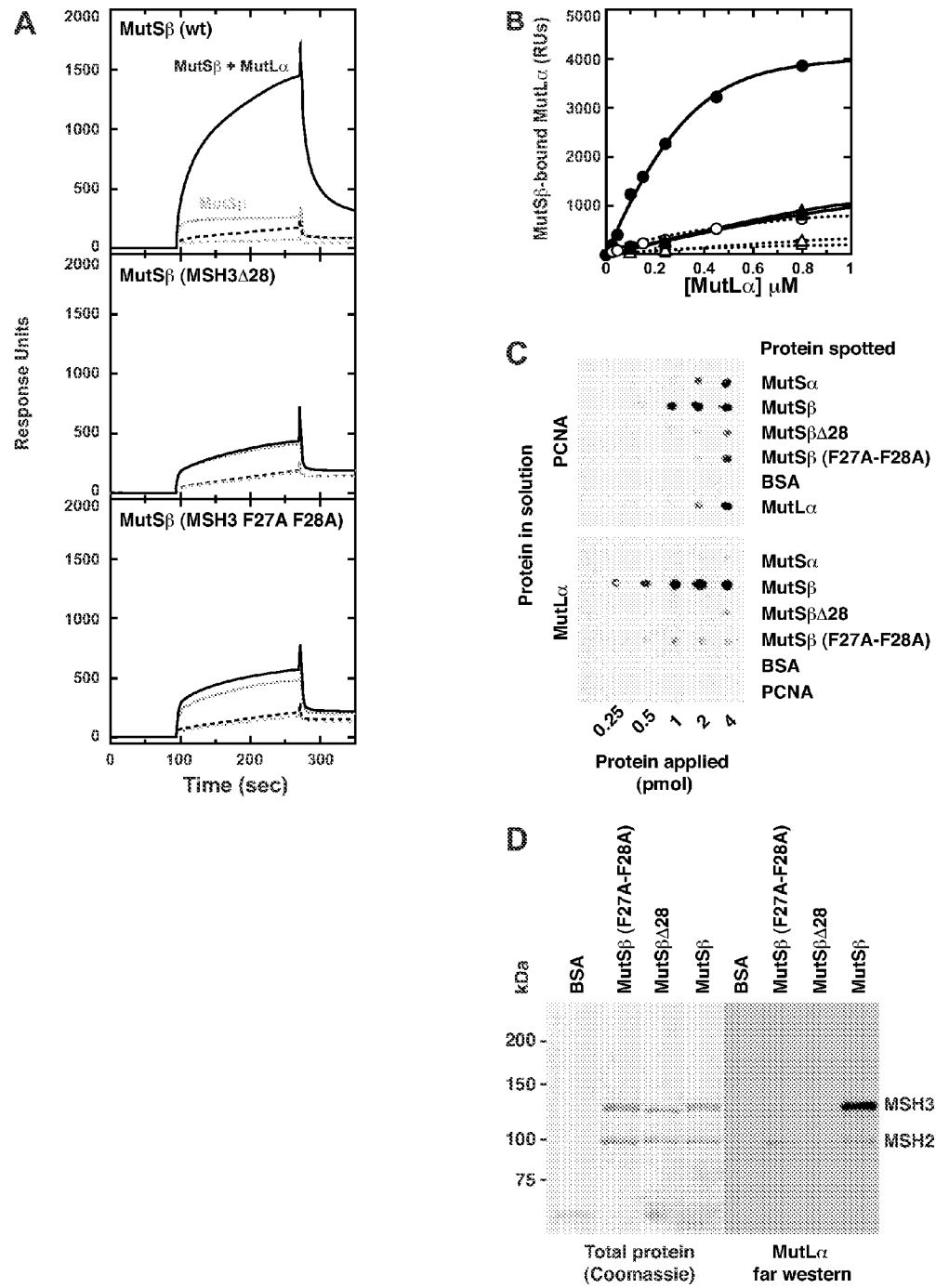
FIG. 2A depicts MutLα-MutSβ-DNA ternary complex formation scored by surface plasmon resonance spectroscopy (SPRS) using I/D heteroduplex (solid lines) or homoduplex (dashed lines) DNA.
FIG. 2B is a graph showing binding of to MutLα to MutSβ or MutSβ variants (MutSβΔ28 and MutSβ-F27A-F28A) as a function of MutLα concentration.
FIG. 2C is a photograph of a nitrocellulose membrane showing binding of PCNA or MutLα to MutSβ or variants thereof, detected by far-western analysis.
FIG. 2D includes photographs of SDS gel-resolved subunits MutSβ variants stained with Coomassie (left panel), or bound to MutLα, as detected by far western analysis.

Interaction between MutS and MutL homologs has been documented in several systems (3, 4), but the nature of the human MutLα-MutSβ complex has not been addressed. We have therefore used SPRS to examine the capacity of MutSβ and its PIP box mutants to support formation of a MutLα-MutSβ-DNA ternary complex. With reference to FIG. 2A, ATP-dependent assembly of the MutLα-MutSβ-DNA ternary complex was scored by SPRS using a 200 bp -TG- I/D heteroduplex (solid lines) or homoduplex (dashed lines) DNA. The upper panel shows mass bound upon flow of 0.10 µM MutSβ alone (grey) or a mixture of 0.10 µM MutSβ and 0.24 µM MutLα (black) over heteroduplex or homoduplex in the presence of 1 mM ATP. Similar analyses were performed with MutSβΔ28 (middle panel) and MutSβ-F27A-F28A. As shown in FIG. 2A, in the presence of ATP-Mg$^{+2}$ MutSβ forms specific but short-lived complexes with the 200 bp -TG- I/D heteroduplex described above. Inclusion of both MutLα and MutSβ resulted in a substantial increase in DNA-bound mass (FIG. 2A), indicative of ternary complex formation. This mass increase was not observed in the absence of ATP (not shown), and we were unable to detect DNA binding by MutLα alone (not shown). The latter results are consistent with previous findings that assembly of ternary complexes involving MutL and MutS homologs is ATP-dependent and that DNA binding by MutL homologs is limited at physiological ionic strength (17, 25, 35-38). The lifetime of the ternary complex is also short, with 80% dissociating with a $t_{1/2}$ of 7s. The apparent affinity of MutLα for DNA-bound MutSβ was estimated from the MutLα dependence of the mass increase over and above that observed with MutSβ alone (0.1 μM). As shown in FIG. 2B, results fit well to a rectangular hyperbola with a $K_d$ of 0.4 μM. Apparent affinity of MutLα for MutSβ (circles), MutSβΔ28 (squares) or MutSβ-F27A-F28A (triangles) was determined from SPRS experiments like those described above, but in which the concentration of MutLα was varied as shown in the presence of 0.10 μM MutSβ. Data were fit to a hyperbola by nonlinear least squares regression to yield an apparent $K_d$ of 0.40 μM on heteroduplex DNA (closed symbols). Complex formation on homoduplex DNA (open symbols) was not saturable.

Figure 6:
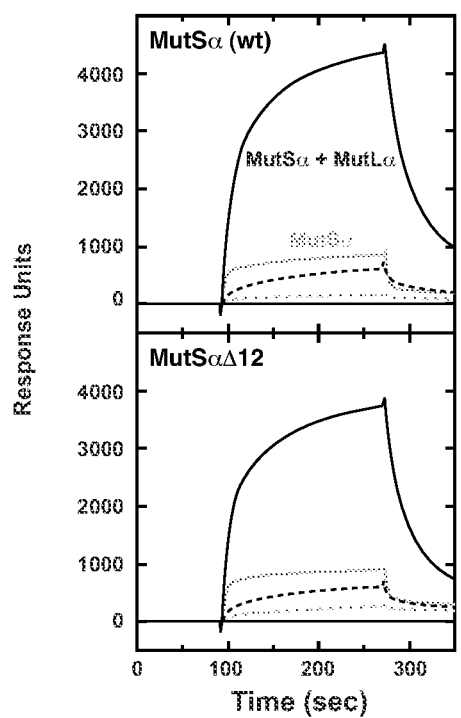
FIG. 6 depicts MutLα-MutSα-DNA ternary complex formation scored by SPRS using I/D heteroduplex (solid lines) or homoduplex (dashed lines) DNA and wild type MutSα (top panel) or PIP box mutant MutSαΔ12.

To our surprise, substitution of MutSβΔ28 or MutSβ-F27A-F28A (FIG. 2A, middle and lower panels) for MutSβ abolished ternary complex formation, indicating that MSH3 PIP box mutations compromise the ability of DNA-bound MutSβ to interact with MutLα. In contrast, deletion of the PIP box motif of MutSα, while severely attenuating the capacity of MutSα to associate with PCNA (21), does not alter the ability of the MSH2-MSH6 heterodimer to support ternary complex formation with MutLα and heteroduplex DNA (FIG. 6). MutSαΔ12, a PIP box mutant of MutSα, was also evaluated for its ability to interact with MutLα. Assembly of an ATP-dependent MutLα·MutSα·heteroduplex ternary complex was scored as in FIG. 2A. With reference to FIG. 6, mass bound upon flow of 0.20 μM MutSα alone (grey) or a mixture of 0.20 μM MutSα and 0.20 μM MutLα (black) over heteroduplex (solid lines) or homoduplex (dashed lines) DNA in a buffer (Experimental Procedures) containing 0.25 mM ATP is shown for wild type MutSα (Top panel) and MutSαΔ12 (Bottom panel).

To assess the interaction of MutSβ with MutLα by an independent method, we employed far-western analyses (Experimental Procedures), wherein the indicated amounts of each protein was spotted on a nitrocellulose membrane, and incubated at 4° C. overnight with 0.18 μM of either PCNA or MutLα in solution, followed by immunochemical detection of membrane-bound PCNA or MutLα (FIG. 2C). Interaction of MutSβ variants with PCNA and MutLα was also assessed independently by far western analysis. PCNA and MutLα were detected immunochemically. As shown in FIG. 2C (top panel), complexes of PCNA with MutSα, MutSβ, and MutLα can be detected by this method, confirming previous findings (14, 26). However, binding of PCNA to MutSβΔ28 and MutSβ-F27A-F28A to PCNA was substantially reduced compared that of wild type MutSβ. When MutLα was in solution (FIG. 2C, bottom panel), robust complex formation with membrane-bound MutSβ was observed. However, binding of MutLα to both MutSβΔ28 and MutSβ-F27A-F28A was severely compromised. While PCNA in solution is able to associate with membrane-bound MutLα, such an interaction was not observed in the converse experiment wherein MutLα was in solution and PCNA was membrane-bound. The reason for this difference is not clear, but it is possible that PCNA binding to the membrane may occlude access to its MutLα-binding surface. An alternate possibility is that the α-MLH1 antibody used to probe for presence of PCNA-bound MutLα may compete with PCNA for a common binding site. MutLα in solution also interacts poorly with nitrocellulose-bound MutSα, possibly due to membrane occlusion effects. Taken together with the SPRS ternary complex observations described above, these far-western results indicate that the MutSβ motif responsible for its interaction MutLα resides at least in part within the N-terminal 28 residues of MSH3 and includes Phe-27 and Phe-28.

Interaction of MutLα with separated MSH2 or MSH3 subunits of MutSβ or its variants (BSA served as a negative control) was assayed by far western analysis after subunit resolution by SDS-PAGE (Experimental Procedures). Membrane treatment was as described above in the preceding paragraph, except that incubation was with 0.09 μM of MutLα. In fact, strong MutLα interaction with the MSH3 subunit of MutSβ was directly demonstrable by far western analysis of membrane transfers from SDS gel-resolved MutSβ subunits, and this interaction was abolished by the PIP box mutations described above (FIG. 2D).

Example 3

Effects of PCNA on MutLα binding to MutSβ and MutSα

Figure 3:
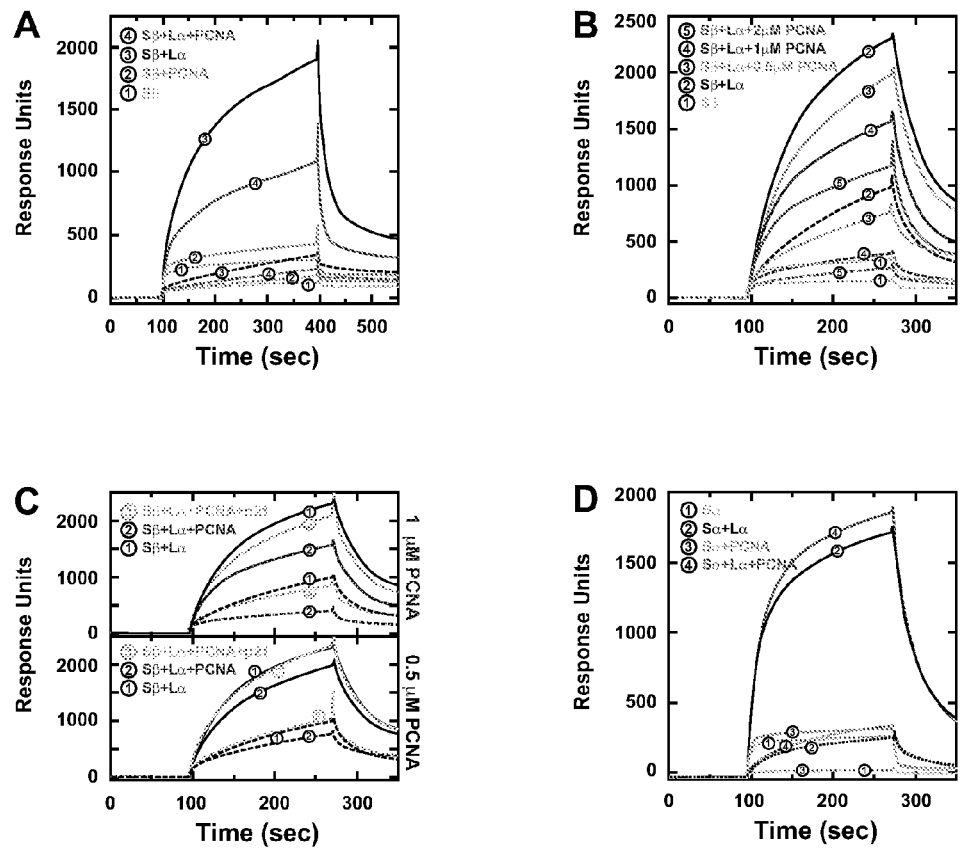
FIG. 3A-C show the results of SPRS analysis of the effect of PCNA on DNA-MutSβ-MutLα ternary complex formation at 2.0 µM PCNA or in the absence of PCNA (FIG. 3A), in the presence of from 0-2.0 µM PCNA (FIG. 3B), in the presence of a molar excess of p21$^{CIP1}$ (FIG. 3C). Solid and dashed lines represent results using dinucleotide I/D heteroduplex or control homoduplex DNAs, respectively.
FIG. 3D shows the results of SPRS analysis, which indicate that PCNA forms a DNA-MutSα-PCNA-MutLα quaternary complex in the presence of DNA, MutSα, and MutLα. Experiments using dinucleotide I/D heteroduplex or control homoduplex DNAs are represented by solid and dashed lines, respectively.

The simplest interpretation of Example 2 is overlap of MSH3 binding sites for PCNA and MutLα, an idea that predicts competition of the two proteins for complex formation with MutSβ. To test this possibility we used SPRS to examine effects of PCNA on DNA-MutSβ-MutLα ternary complex formation. The results, presented in FIG. 3, show that PCNA and MutLα compete for binding to MutSβ but not to MutSα. The effect of PCNA on formation of DNA-MutSβ-MutLα and DNA-MutSα-MutLα ternary complexes was evaluated by SPRS using a sensor chip derivatized with 200 bp -TG- I/D heteroduplex (solid lines) or control homoduplex (dashed lines) DNA (FIG. 3A) Sensorgram profiles show mass response units upon flow of solutions containing 1 mM ATP and: 0.10 μM MutSβ (curve 1); 0.10 μM MutSβ and 0.24 μM MutLα (curve 3); 0.10 μM MutSβ and 2.0 μM PCNA (curve 2); and 0.10 μM MutSβ, 0.24 μM MutLα and 2.0 μM PCNA (curve 4). Inhibition of ternary complex formation as a function of PCNA concentration was measured by monitoring mass bound when solutions containing 0.050 μM MutSβ (curve 1), or a mixture composed of 0.050 μM MutSβ, 0.050 μM MutLα, and one of the following: 0 (curve 2), 0.50 (curve 3), 1.0 (curve 4), or 2.0 μM (curve 5) PCNA were allowed to flow over the sensor chip in the presence of 0.25 mM ATP and 125 mM KCl. (FIG. 3B). Effect of p21 on PCNA-dependent inhibition of DNA-MutSβ-MutLα ternary complex formation (FIG. 3C) was assessed as in (FIG. 3B) by flowing a mixture of 0.050 μM MutSβ, 0.050 μM MutLα, and 0.25 mM ATP (curve 1, Top and Bottom panels) or the same mixture supplemented with one of the following: 1.0 μM PCNA (curve 2, Top panel), 0.50 μM PCNA (curve 2, Bottom panel), 1.0 μM PCNA and 6.0 μM p21 (curve 3, Top panel), or 0.50 μM PCNA and 6.0 μM p21 (curve 3, Bottom panel). SPRS experiments shown in FIG. 3D were as in (FIG. 3A), but with 0.20 μM MutSα (curve 1); 0.20 μM MutSα and 0.20 μM MutLα (curve 2); 0.20 μM MutSα and 1.6 μM PCNA (curve 3); 0.20 μM MutSα, 0.20 μM MutLα and 1.6 μM PCNA (curve 4).

Addition of 2.0 μM PCNA to a solution containing MutSβ results in an increase in mass bound to the sensor surface consistent with MutSβ-PCNA complex formation (FIG. 3A). Addition of the same amount of PCNA to a mixture of MutSβ and MutLα results in a substantial decrease in chip-bound mass as compared with that in the absence of the clamp (FIG. 3A, compare red and black lines), indicating that PCNA inhibits the assembly of the DNA-MutSβ-MutLα ternary complex. PCNA inhibition of this reaction increases with increasing PCNA concentration (FIG. 3B), an effect that is reversed by presence of a molar excess of the PCNA-binding cell cycle regulator $p21^{CIP1}$ (FIG. 3C).

As discussed above, unlike MutSβ PIP box mutants, MutSαΔ12, which lacks the MSH6 PCNA interaction motif, is proficient in assembly of the DNA-MutSα-MutLα ternary complex (FIG. 6). It might therefore be expected that assembly of the MutSα ternary complex would be refractory to the inhibitory effect of PCNA. Indeed, presence of PCNA in solutions containing MutSα, MutLα, and ATP resulted in a further increase in DNA-bound mass (FIG. 3D), indicating the formation of a DNA-MutSα-PCNA-MutLα quaternary complex. Interestingly, the resultant mass increase is ~2-3 fold greater than that due to PCNA association with the DNA-MutSα complex, which may indicate that MutLα promotes multiple MutSα loading events or that PCNA may interact with both MutSα and MutLα components of the ternary complex (FIG. 2C) (13). By contrast, MutSαΔ12 fails to support formation of a DNA-MutSαΔ12-PCNA-MutLα quaternary complex (not shown), indicating that initial association of PCNA with the DNA-MutSα-MutLα ternary complex occurs via multiply loaded MutSα molecules. These data suggest that in contrast to MutSβ, MutSα has distinct binding sites that can be simultaneously occupied by MutLα and PCNA.

Example 4

Figure 4:
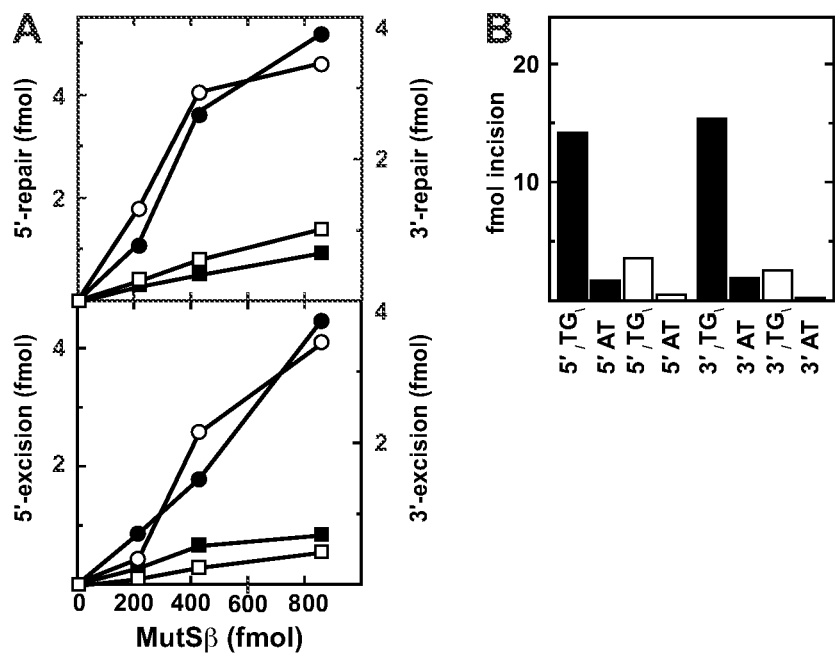
FIG. 4A depicts repair of 5'- (closed symbols) or 3'- (open symbols) dinucleotide I/D heteroduplex in nuclear extracts scored as a function of exogenously added MutSβ (circles) or MutSβΔ28 (squares) (Top); excision on 5'- and 3'-substrates was scored by NheI-resistant gap formation assay in the absence of exogenous dNTPs as a function of added MutSβ and MutSβΔ28 (Bottom).
FIG. 4B compares the ability of MutSβ (black bars) and MutSβΔ28 (white bars) (100 ng or 430 fmol) to support MutLα endonuclease activation on 5'- and 3'-TG- I/D heteroduplex or A-T homoduplex DNAs.

The MSH3 PIP Box Required for MutLα Endonuclease Activation and Bidirectional Mismatch-Provoked Excision and Repair We have previously shown that MutSαΔ12, although unable to associate with PCNA, retains mismatch recognition activity, supports MutLα endonuclease activation, and is as active as the wild type protein in mismatch-provoked excision. The mutant does however display a partial defect in 5'- but not 3'-directed mismatch repair (21). To determine the functional consequences of disruption of the MSH3 PIP box motif in MutSβ, we examined the activities of MutSβ PIP box mutants in nuclear extracts of MSH2$^{-/-}$ RL95-2 cells, and in a purified system that scores MutLα endonuclease activation. With reference to FIG. 4A, top panel, repair of 5'-(closed symbols) or 3'- (open symbols) dinucleotide I/D heteroduplex (Experimental Procedures) was scored in nuclear extracts of MSH2$^{-/-}$ RL95-2 cells as a function of exogenously added MutSβ (circles) or MutSβΔ28 (squares). Excision on 5'- and 3'-substrates was scored by NheI-resistant gap formation assay (33) in RL95-2 extracts in the absence of exogenous dNTPs as a function of added MutSβ and MutSβΔ28 (FIG. 4A, bottom panel). As judged by extract assay, MutSβΔ28 displays a severe defect in 5'- and 3'-excision and repair as compared with the wild type protein (FIG. 4A). In FIG. 4B, MutSβ (black bars) and MutSβΔ28 (white bars) (100 ng or 430 fmol) were compared for their ability to support MutLα endonuclease activation (16) on 5'- and 3'-TG- I/D heteroduplex or A-T homoduplex DNAs (Experimental Procedures). Results shown are corrected for background observed in the absence of MutSβ, MutLα, RFC, and PCNA. Unlike the wild type protein, the capacity of this truncation mutant to activate the MutLα endonuclease is also severely attenuated (FIG. 4B). Initial rates of MutSβ-dependent MutLα endonucleolytic activity supported by MutSβ-F27A-F28A are also ~3-4 fold lower than the wild type protein (data not shown). Thus, unlike MSH6, integrity of the MSH3 PIP box is required for mismatch repair.

Example 5

Solution Conformations of MutSβ and the MutSβ-PCNA Complex

Figure 5:
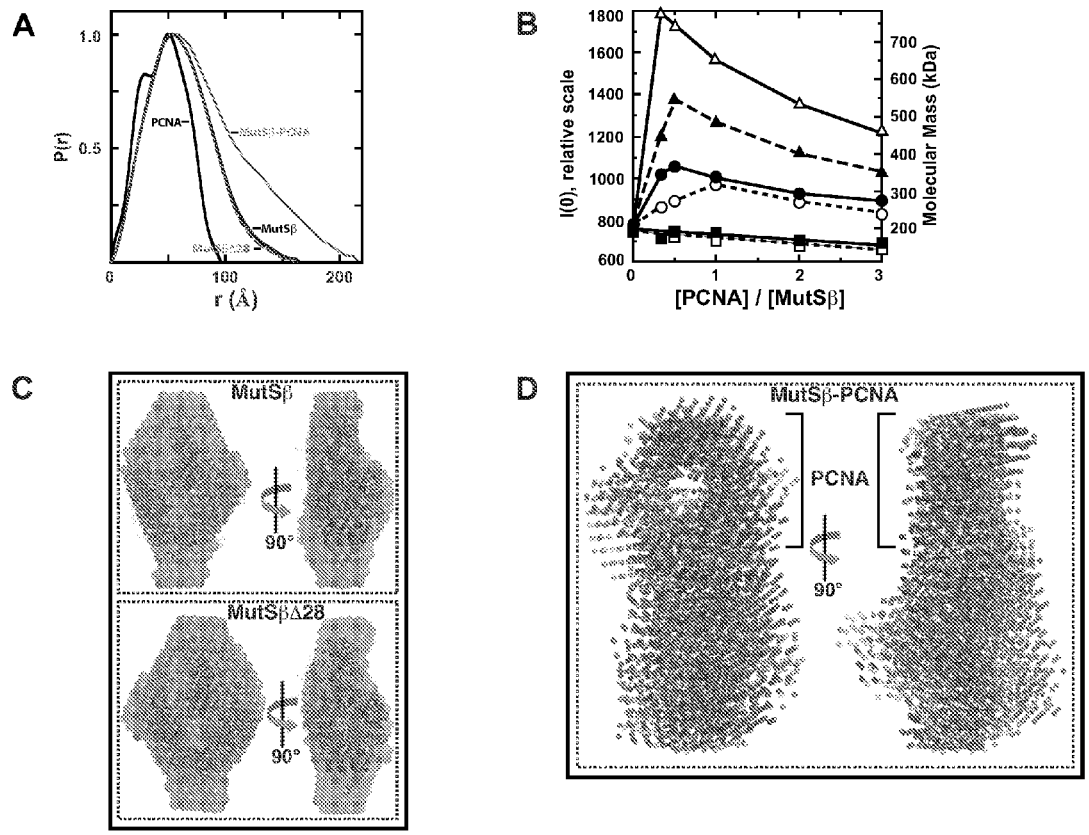
FIG. 5A shows normalized pair distribution (P(r)) plots for MutSβ, MutSβΔ28, an equimolar mixture of MutSβ and PCNA, and PCNA alone (reproduced from (21)) derived by indirect Fourier transform (49) of solution small-angle X-ray scattering (SAXS) data.
FIG. 5B Experimentally determined forward scattering intensities I(0) plotted as a function of PCNA:MutSβ (closed circles) or PCNA:MutSβΔ28 (closed squares) molar ratio; theoretical dependence of I(0) on PCNA:MutSβ molar ratio was calculated for scenarios that assume formation of the stoichiometric complexes MutSβ-PCNA (318 kDa) (open circles), (MutSβ)$_2$-PCNA (550 kDa) (closed triangles) or (MutSβ)$_3$-PCNA (782 kDa) (open triangles); I(0) values for PCNA mixtures with MutSβΔ28 (open squares) are also shown with the assumption of no interaction. Molecular masses corresponding to I(0) values are indicated on the right vertical axis.
FIG. 5C Ab initio shape reconstructions of MutSβ and MutSβΔ28 were performed from SAXS data.
FIG. 5D Ab initio shapes of the MutSβ-PCNA complex were generated as described above from experimental scattering data collected for 1:1 molar mixtures of MutSβ and PCNA.

FIG. 7A shows solution X-ray scattering data and linear portions of Guinier plots for MutSβ, MutSβΔ28, PCNA, and an equimolar mixture of MutSβ and PCNA. The corresponding pairwise interatomic distances distributions (P(r)) were derived from scattering profiles by indirect Fourier transform (FIG. 5A). Results of small-angle X-ray scattering studies of MutSβ and the MutSβ-PCNA complex are presented in FIG. 5A-5D.

With reference to FIG. 5A, normalized pair distribution (P(r)) plots for MutSβ, MutSβΔ28, an equimolar mixture of MutSβ and PCNA, and PCNA alone, reproduced from (21) were derived by indirect Fourier transform (49) of solution scattering data. In FIG. 5B, stoichiometry of the MutSβ-PCNA interaction was determined (Experimental Procedures) from experimentally determined forward scattering intensities I(0) plotted as a function of PCNA:MutSβ (closed circles) or PCNA:MutSβΔ28 (closed squares) molar ratio. The theoretical dependence of I(0) on PCNA:MutSβ molar ratio was calculated for scenarios that assume formation of the stoichiometric complexes MutSβ-PCNA (318 kDa) (open circles), (MutSβ)$_2$-PCNA (550 kDa) (closed triangles) or (MutSβ)$_3$-PCNA (782 kDa) (open triangles) (Experimental Procedures). The expected I(0) values for PCNA mixtures with MutSβΔ28 (open squares) are also shown with the assumption of no interaction. Molecular masses corresponding to I(0) values (FIG. 7B) are indicated on the right vertical axis. Ab initio shape reconstructions of MutSβ and MutSβΔ28 were performed from SAXS data as described (21). Envelopes shown represent an average of 10 independent shape reconstructions. Due to non-availability of a MutSβ crystal structure, the MutSαΔ341-DNA complex structure (40) is superimposed on the MutSβ SAXS envelope for size reference. Ab initio shapes of the MutSβ-PCNA complex were generated as described above from experimental scattering data collected for 1:1 molar mixtures of MutSβ and PCNA. Eight independent ab initio shapes are shown manually superimposed on each other. Despite the low resolution of these models, a central channel of dimensions similar to that of PCNA is clearly defined and was used to align the individual reconstructions. See also FIG. 7 and Table 2.

Figure 7:
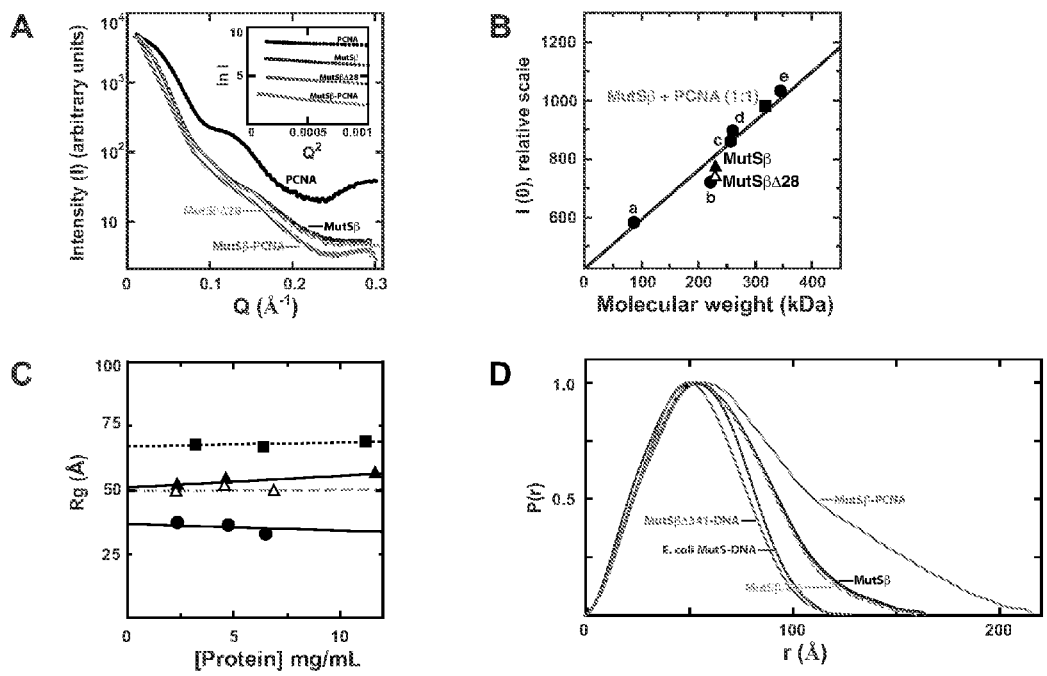
FIG. 7 depicts SAXS properties of MutSβ and MutSβ-PCNA.

With reference to FIG. 7, scattering intensities (I) versus the scattering vector Q are shown for MutSβ, MutSβΔ28, an equimolar mixture of MutSβ and PCNA, and PCNA alone (reproduced from (21)) (FIG. 7A). Guinier plots (ln I vs. Q$^2$) (2), linear portions of which are shown (inset), were derived from scattering profiles and were used to determine radii of gyration (Table 1). In FIG. 7B, forward scattering intensities I(0) (intensity at θ=0°) for MutSβ (closed triangle) MutSβΔ28 (open triangle) and an equimolar mixture of MutSβ and PCNA were derived from concentration-normalized scattering data by the Guinier approximation (32) and are plotted as a function of the molecular mass of each molecule (41). Data are plotted alongside results reproduced from Iyer et al. (21) for (a) PCNA, (b) MutSαΔ341, (c) MutSαΔ12, (d) MutSα, (e) MutSα·PCNA. FIG. 7C shows dependence of apparent Rg on protein concentration for MutSβ (closed triangles), MutSβΔ28 (open triangles), and the MutSα·PCNA complex (closed squares). Data for PCNA (closed circles) are reproduced from Iyer et al. (21). MutSβ, MutSαΔ28, and MutSβ·PCNA displayed negligible interparticle association. (FIG. 7D) P(r) plots from FIG. 5A, excluding that for PCNA, are reproduced alongside pairwise interatomic distances calculated from the crystal structures of MutSαΔ341·DNA (40) and *E. coli* MutS·DNA (39).

Table 2 summarizes the model-independent structural parameters R$_g$ and D$_{max}$ obtained from these experiments. As observed previously for MutSα (21), the P(r) distributions for MutSβ and MutSβΔ28 are skewed toward larger r values indicating that the conformations of these two heterodimers are significantly more elongated than the published structures of truncated forms of MutS homologs (FIG. 7D) (39, 40). Addition of one PCNA trimer equivalent to MutSβ results in a further skewing of the P(r) distribution towards higher values.

TABLE 2

Estimation of possible molecular constituents of MutSβ-PCNA mixtures under conditions of MutSβ molar excess. Experimentally measured forward scattering intensity I(0) data are higher than expected when the PCNA:MutSβ molar ratio is less than 1 (FIG. 5B), indicative of the presence of species of molecular mass greater than that of the 318 kDa MutSβ•PCNA complex. Potential contributions of the divalent (MutSβ)$_2$•PCNA and trivalent (MutSβ)$_3$•PCNA complexes was estimated from the difference between experimentally measured and expected I(0) values (Experimental Procedures). Two scenarios are considered: (1) mixture of MutSβ•PCNA and (MutSβ)$_2$•PCNA, and (2) mixture of MutSβ•PCNA and (MutSβ)$_3$•PCNA. Complex mixtures containing all three species were not considered.

| | | | Possible species | | | |
|---|---|---|---|---|---|---|
| | | | MutSβ•PCNA + (MutSβ)$_2$•PCNA | | MutSβ•PCNA + (MutSβ)$_3$•PCNA | |
| PCNA/MutSβ molar ratio | Expected I(0)$^a$ | Observed I(0) | % MutSβ•PCNA (318 kDa) | % (MutSβ)$_2$•PCNA (550 kDa) | % MutSβ•PCNA (318 kDa) | % (MutSβ)$_3$•PCNA (782 kDa) |
| 0.33 | 857 (267 kDa)$^b$ | 1020 (346 kDa)$^b$ | 79 | 21 | 90 | 10 |
| 0.5 | 869 (282 kDa)$^b$ | 1053 (364 kDa)$^b$ | 87 | 13 | 93 | 7 |

$^a$If preferred stoichiometry is MutSβ•PCNA
$^b$Molecular masses corresponding to the I(0) values are shown in parantheses, and were derived from FIG. S2B.

As noted above (Table 1), gel filtration studies showed an increase in Stokes' radius for MutSβ from 64 to 74 Å due to formation of the MutSβ-PCNA complex. The similar but distinct conformational parameter, $R_g$, measured by SAXS also increases when one PCNA equivalent is added to MutSβ, an effect that is not observed with MutSβΔ28 (Table 1). The SAXS data also permit extraction of forward scattering intensity I(0), which is a linear function of molecular mass (41) (FIG. 7B). I(0) values determined for 1:1 mixtures of the MutSβ and PCNA proteins are substantially greater than those for either of the individual molecules (FIG. 7B) and are consistent with expected molecular mass of a 1:1 MutSβ-PCNA trimer complex (318 kDa). By contrast, an equimolar mixture of MutSβΔ28 and PCNA yields a significantly lower value for I(0), indicating that the two proteins fail to interact (see below).

Given the trivalent nature of PCNA (42), it is potentially possible to assemble MutSβ-PCNA complexes of differing stoichiometries: MutSβ-PCNA, (MutSβ)$_2$-PCNA, and (MutSβ)$_3$-PCNA, with monovalent complexes favored under conditions of PCNA excess. As discussed above, the stoichiometry of this interaction determined by equilibrium gel filtration and SPRS is 1 MutSβ heterodimer per PCNA homotrimer. Because complex formation in both of these procedures was measured under conditions where PCNA was in excess, these experiments are insensitive to the formation of potential (MutSβ)$_2$-PCNA, and (MutSβ)$_3$-PCNA assemblies. To address this issue, we determined I(0) values for PCNA-MutSβ mixtures as a function of molar ratio under conditions where the concentration of each protein was well above the $K_d$ for binary complex formation. As shown in FIG. 5B, the experimental maximum I(0) occurs at a PCNA:MutSβ molar ratio of 0.5, indicative of presence of multivalent species. Comparison of experimentally determined values to those calculated for mixtures of (MutSβ)$_2$-PCNA and MutSβ-PCNA, or (MutSβ)$_3$-PCNA and MutSβ-PCNA demonstrated that the MutSβ-PCNA complex is the favored species at PCNA:MutSβ molar ratios ≥1, but as many as 20% of the complexes are multivalent at lower values (Table 2). Furthermore, I(0) does not increase as a function of the MutSβΔ28:PCNA ratio (FIG. 5B), a finding that independently confirms the PCNA interaction defect of this MutSβ variant.

Ab initio shape reconstructions for MutSβ and the MutSβ-PCNA complex from SAXS data—Model-independent $D_{max}$ values (Table 1, (21)) indicate that the MutSβ conformation in solution ($D_{max}$=165 Å) is more extended than MutSαΔ341 ($D_{max}$=140 Å) but more compact than MutSα ($D_{max}$=202 Å). Since a crystal structure of MutSβ is not available, SAXS results described above were used to generate low-resolution conformational models (43) of the heterodimer, as well as its complex with PCNA. The validity of the models was assessed using the crystal structures of the human MutSαΔ341-DNA complex (40) and PCNA (42). Ab initio envelopes of MutSβ and MutSβΔ28 (FIG. 5C) accommodate superimposition of the crystal structure of the MutSαΔ341-DNA complex, and display additional mass that presumably corresponds to portions of MutSβ that do not share sequence or conformational homology with MutSαΔ341.

As noted above, addition of one trimer equivalent of PCNA to MutSβ results in a P(r) plot that is skewed towards higher interatomic distances by ~55 Å, an effect that is manifested as a substantial increase in $D_{max}$ (FIG. 5A, Table I). However, the maximum P(r) value for the MutSβ-PCNA complex occurs at an r value (56 Å) that is nearly identical to that for MutSβ alone (54 Å). These results suggest that the MutSβ-PCNA complex adopts an "extended" end-to-end conformation rather than a stacked arrangement wherein the DNA-binding channels of the two proteins are juxtaposed, since the latter conformer would be expected to display a P(r) maximum at a substantially higher r value (21). In fact, ab initio shapes generated from SAXS data are consistent with an end-to-end association of MutSβ and PCNA (FIG. 5D), with the ring shape of PCNA being clearly defined in the low resolution models along with substantial associated mass consistent with presence of a MutS homolog dimer equivalent. By contrast to the variety of extended ab initio shapes obtained for the MutSα-PCNA complex (21), low resolution MutSβ-PCNA models are strikingly similar (FIG. 5D), suggesting that there is limited variability between individual MutSβ-PCNA conformers in solution.

Example 6

(Prophetic) Screening libraries for ability to inhibit interaction of MutSα/β and MutLα

High throughput assay for ternary complex formation. Streptavidin-coated polystyrene plates in 96-well format (Greiner Bio-One) will be derivatized with a biotin end-labeled 200 bp heteroduplex (or control homoduplex) DNA, which we prepare by a PCR, strand separation, hybridization procedure (20). MutLα-MutSα/MutSβ-heteroduplex ternary complex assembly is ATP-dependent, and the resultant complexes are dynamic, apparently capable of movement along the helix (50, 17, 19). Because such complexes can be trapped on a linear heteroduplex if both DNA ends are blocked by bound protein (17, 19), blocking of the free heteroduplex terminus distal to the polystyrene surface may enhance ternary complex signal for immunological or fluorescence resonance energy transfer (FRET) detection purposes (see below). For FRET-based assay, this can be accomplished by placement of an EcoRI site near the free terminus and use of hydrolytically dead mutant of EcoRI endonuclease (EcoRIE$_{111}$Q) that binds to d(GAATTC) sites with an affinity of $10^{13}$ M$^{-1}$ at 150 mM NaCl (57). An alternate possibility for immunological assay involves heteroduplex preparation with a biotin label at one end and fluorescein at the other, coupled with use of commercial anti-fluorescein antibody to block the dye-tagged heteroduplex terminus. Initial experiments will utilize a 200 bp -TG-"loopout" heteroduplex, which is readily recognized by both MutSα and MutSβ, with an otherwise identical homoduplex as control (50).

Immunological assay will rely on demonstration of mismatch and MutSα/MutSβ-dependent assembly of a complex, that after rinsing the reaction wells, yields a signal upon incubation with rabbit anti-peptide or mouse monoclonal anti-hPMS2 or anti-hMLH1 antibody. Immune complexes will be scored by luminescence assay after reaction with an appropriate peroxidase-conjugated anti-rabbit or anti-mouse antiserum. Although MutLα-MutSα/MutSβ-heteroduplex ternary complex formation could result in occlusion of some hPMS2 or hMLH1 antigenic sites, we are not overly concerned about this problem because commercially available anti-hPMS2 or anti-hMLH1 antibodies target a number of different epitopes.

FRET assay will be based on the tetracysteine/biarsenical chemistry developed by Tsien and colleagues for specific fluorescent labeling of proteins (58, 59). We have already tagged hMSH2 (N-terminal derivative) and hMLH1 (N-terminal and C-terminal derivatives) with an optimized tetracysteine peptide (FLNCCPGCCMEP) (SEQ ID NO: 7) that is highly reactive with the biarsenical fluorogenic probes 4',5'-bis(1,3,2-dithiarsolan-2-yl)fluorescein (FlAsH, FRET donor) and 4,5-bis(1,3,2-dithiarsolan-2-yl)-resorufin (ReAsH, FRET acceptor). Our intent is to utilize FlAsH-derivatized hMutSα/hMutSβ and ReAsH-derivatized hMutLα, or other appropriate FRET pair, for high throughput assay of ternary complex formation.

Another approach to assay development would be to attach a 200-bp heteroduplex DNA substrate prepared by PCR such that the 5'-end of the top strand contains a biotin tag, and the 5'-end of the bottom strand has a fluorescein label to a standard 96-well ELISA plate coated with goat anti-fluorescein antibody. After blocking the non-specific DNA and protein binding sites on the plate, the double tagged DNA substrate will be attached to the plate surface via the fluorescein label. The free biotin tagged end will be blocked by recombinant monovalent avidin. The DNA substrate will be incubated with MutSβ, MutLα and ATP, unbound protein will be washed off. MutSβ-dependent recruitment of MutLα will be detected immunologically as detailed below. The presence of two end-blocks on the DNA substrate will stabilize and permit detection of DNA·MutSβ·MutLα complexes that may otherwise be short lived due to rapid dissociation off a free DNA end. MutLα will be detected by incubation with a mouse or rabbit anti-MLH1 antibody, followed by incubation with horseradish peroxidase labeled anti-mouse or anti-rabbit secondary antibody. The amount of MutLα present will be inferred by colorimetric quantitation of peroxidase activity using tetramethylbenzidine as substrate. This is a rapid assay that can be used to screen libraries of small molecules for their ability to inhibit recruitment of MutLα to DNA-bound MutSβ. A parallel assay will be set up wherein MutSα is used instead of MutSβ, and will be used to identify molecules that are without effect on the MutSα-dependent recruitment of MutLα.

A high throughput assay described above will be used to assay libraries of small molecules. For example, a proof of principle small molecule inhibitor screen could be performed using the 1364 compound NCI Diversity Set II small molecule inhibitor library. These compounds will be screened in sets of 5-10. Those responsible for inhibitory hits at <100 μM will be identified and individually screened for their ability to inhibit hMutLα-hMutSα-heteroduplex and hMutLα-hMutSβ-heteroduplex complex assembly as judged by plate reader screen and by independent BIAcore assay (50, 17). Because of their potential therapeutic value, we are particularly interested in the latter class of inhibitor, but inhibitors that block formation of either or both ternary complex would be of potential interest to the MMR field.

The molecules identified in such a screen may be further characterized by a modified far-western assay designed to detect direct interaction between MutSβ and MutLα. A defined amount of MutSβ will be spotted in each well of a 96-well nitrocellulose bottom microplate. After non-specific protein binding sites have been blocked with a nonspecific protein such as casein, the wells will be incubated with a solution containing MutLα. Presence of MutLα will be detected immunologically as detailed above. Molecules that directly inhibit binding of MutLα to MutSβ will be identified by this method.

Molecules that have been identified by the rapid screens described above will be further tested for their capacity to inhibit MutSβ-dependent activation of MutLα endonucleolytic function in in vitro assays on heteroduplex DNA substrates. These molecules will then be tested for their capacity to inhibit bidirectional mismatch excision and repair of a variety of heteroduplex substrates (some of which will be prepared from triplet repeats) in in vitro assays composed of either purified mismatch repair proteins extracts of mismatch repair capable human cells. Kinetics of binding/inhibition will be measured by surface plasmon resonance spectroscopy (Biacore).

Each reference cited herein is incorporated by reference in its entirety.

CITED REFERENCES

1. Kolodner, R. D., and Marsischky, G. T. (1999) *Curr. Opin. Genet. Dev.* 9, 89-96
2. Kunkel, T. A., and Erie, D. A. (2005) *Annu. Rev. Biochem.* 74, 681-710
3. Iyer, R. R., Pluciennik, A., Burdett, V., and Modrich, P. L. (2006) *Chem. Rev.* 106, 302-323
4. Hsieh, P., and Yamane, K. (2008) *Mech. Ageing Dev.* 129, 391-407
5. Li, G. M. (2008) *Cell Res.* 18, 85-98
6. Peltomaki, P. (2003) *J. Clin. Oncol.* 21, 1174-1179
7. Stojic, L., Brun, R., and Jiricny, J. (2004) *DNA Repair (Amst)* 3, 1091-1101
8. Zhang, N., Lu, X., Zhang, X., Peterson, C. A., and Legerski, R. J. (2002) *Mol. Cell. Biol.* 22, 2388-2397

9. Zhao, J., Jain, A., Iyer, R. R., Modrich, P. L., and Vasquez, K. M. (2009) *Nucleic Acids Res.* 37, 4420-4429
10. Di Noia, J. M., and Neuberger, M. S. (2007) *Annu. Rev. Biochem.* 76, 1-22
11. Brouwer, J. R., Willemsen, R., and Oostra, B. A. (2009) *Bioessays* 31, 71-83
12. Genschel, J., and Modrich, P. (2003) *Mol. Cell.* 12, 1077-1086
13. Dzantiev, L., Constantin, N., Genschel, J., Iyer, R. R., Burgers, P. M., and Modrich, P. (2004) *Mol. Cell.* 15, 31-41
14. Constantin, N., Dzantiev, L., Kadyrov, F. A., and Modrich, P. (2005) *J. Biol. Chem.* 280, 39752-39761
15. Zhang, Y., Yuan, F., Presnell, S. R., Tian, K., Gao, Y., Tomkinson, A. E., Gu, L., and Li, G. M. (2005) *Cell* 122, 693-705
16. Kadyrov, F. A., Dzantiev, L., Constantin, N., and Modrich, P. (2006) *Cell* 126, 297-308
17. Blackwell, L. J., Wang, S., and Modrich, P. (2001) *J. Biol. Chem.* 276, 33233-33240
18. Raschle, M., Dufner, P., Marra, G., and Jiricny, J. (2002) *J. Biol. Chem.* 277, 21810-21820
19. Mendillo, M. L., Mazur, D. J., and Kolodner, R. D. (2005) *J. Biol. Chem.* 280, 22245-22257
20. Flores-Rozas, H., Clark, D., and Kolodner, R. D. (2000) *Nat. Genet.* 26, 375-378
21. Iyer, R. R., Pohlhaus, T. J., Chen, S., Hura, G. L., Dzantiev, L., Beese, L. S., and Modrich, P. (2008) *J. Biol. Chem.* 283, 13310-13319
22. Plotz, G., Welsch, C., Giron-Monzon, L., Friedhoff, P., Albrecht, M., Piiper, A., Biondi, R. M., Lengauer, T., Zeuzem, S., and Raedle, J. (2006) *Nucleic Acids Res.* 34, 6574-6586
23. Clark, A. B., Valle, F., Drotschmann, K., Gary, R. K., and Kunkel, T. A. (2000) *J. Biol. Chem.* 275, 36498-36501
24. Johnson, R. E., Kovvali, G. K., Guzder, S. N., Amin, N. S., Holm, C., Habraken, Y., Sung, P., Prakash, L., and Prakash, S. (1996) *J. Biol. Chem.* 271, 27987-27990
25. Habraken, Y., Sung, P., Prakash, L., and Prakash, S. (1997) *Curr. Biol.* 7, 790-793
26. Kleczkowska, H. E., Marra, G., Lettieri, T., and Jiricny, J. (2001) *Genes Dev.* 15, 724-736
27. Parsons, R., Li, G. M., Longley, M. J., Fang, W. H., Papadopoulos, N., Jen, J., de la Chapelle, A., Kinzler, K. W., Vogelstein, B., and Modrich, P. (1993) *Cell* 75, 1227-1236
28. Genschel, J., and Modrich, P. (2009) *J. Biol. Chem.* 284, 21536-21544
29. Blackwell, L. J., Bjornson, K. P., and Modrich, P. (1998) *J. Biol. Chem.* 273, 32049-32054
30. Genschel, J., Littman, S. J., Drummond, J. T., and Modrich, P. (1998) *J. Biol. Chem.* 273, 19895-19901
31. Gill, S. C., and von Hippel, P. H. (1989) *Anal. Biochem.* 182, 319-326
32. Guinier, A., and Fournet, G. (1955) *Small-angle scattering of x-rays*, John Wiley & Sons, Inc., New York
33. Genschel, J., and Modrich, P. (2006) *Methods in enzymology* 408, 273-284
34. Myszka, D. G. (1999) *J. Mol. Recognit.* 12, 279-284
35. Grilley, M., Welsh, K. M., Su, S. S., and Modrich, P. (1989) *J Biol Chem* 264, 1000-1004
36. Habraken, Y., Sung, P., Prakash, L., and Prakash, S. (1998) *J. Biol. Chem.* 273, 9837-9841
37. Gu, L., Hong, Y., McCulloch, S., Watanabe, H., and Li, G. M. (1998) *Nucleic Acids Res.* 26, 1173-1178
38. Galio, L., Bouquet, C., and Brooks, P. (1999) *Nucleic Acids Res.* 27, 2325-2331
39. Lamers, M. H., Perrakis, A., Enzlin, J. H., Winterwerp, H. H., de Wind, N., and Sixma, T. K. (2000) *Nature* 407, 711-717
40. Warren, J. J., Pohlhaus, T. J., Changela, A., Iyer, R. R., Modrich, P. L., and Beese, L. S. (2007) *Mol. Cell.* 26, 579-592
41. Kratky, O. (1963) *Prog. Biophys. Biophys. Chem.* 13, 105-173
42. Kontopidis, G., Wu, S. Y., Zheleva, D. I., Taylor, P., McInnes, C., Lane, D. P., Fischer, P. M., and Walkinshaw, M. D. (2005) *Proc. Natl. Acad. Sci. U.S.A.* 102, 1871-1876
43. Svergun, D. I., Petoukhov, M. V., and Koch, M. H. (2001) *Biophysical journal* 80, 2946-2953
44. Drummond, J. T., Genschel, J., Wolf, E., and Modrich, P. (1997) *Proc. Natl. Acad. Sci. U. S. A.* 94, 10144-10149
45. Flores-Rozas, H., Kelman, Z., Dean, F. B., Pan, Z. Q., Harper, J. W., Elledge, S. J., O'Donnell, M., and Hurwitz, J. (1994) *Proc. Natl. Acad. Sci. U.S.A.* 91, 8655-8659
46. Dherin, C., Gueneau, E., Francin, M., Nunez, M., Miron, S., Liberti, S. E., Rasmussen, L. J., Zinn-Justin, S., Gilquin, B., Charbonnier, J. B., and Boiteux, S. (2009) *Mol. Cell. Biol.* 29, 907-918
47. Charbonneau, N., Amunugama, R., Schmutte, C., Yoder, K., and Fishel, R. (2009) *Cancer Biol. Ther.* 8, 1411-1420
48. Mendillo, M. L., Hargreaves, V. V., Jamison, J. W., Mo, A. O., Li, S., Putnam, C. D., Woods, V. L., Jr., and Kolodner, R. D. (2009) *Proc. Natl. Acad. Sci. U.S.A.* 106, 22223-22228
49. Svergun, D. I. (1992) *J. Appl. Cryst.* 25, 495-503
50. Iyer R R, Pluciennik A, Genschel J, Tsai M S, Beese L S, & Modrich P (2010) MutLalpha and proliferating cell nuclear antigen share binding sites on MutSbeta. *J. Biol. Chem.* 285:11730-11739, PMC 2857047.
51. Manley K, Shirley T L, Flaherty L, & Messer A (1999) Msh2 deficiency prevents in vivo somatic instability of the CAG repeat in Huntington disease transgenic mice. *Nat. Genet.* 23:471-473.
52. van den Broek W J, Nelen M R, Wansink D G, Coerwinkel M M, te Riele H, Groenen P J, & Wiering a B (2002) Somatic expansion behaviour of the (CTG)n repeat in myotonic dystrophy knock-in mice is differentially affected by Msh3 and Msh6 mismatch-repair proteins. *Hum. Mol. Genet.* 11:191-198.
53. Savouret C, Brisson E, Essers J, Kanaar R, Pastink A, te Riele H, Junien C, & Gourdon G (2003) CTG repeat instability and size variation timing in DNA repair-deficient mice. *EMBO J.* 22:2264-2273, PMC 156074.
54. Wheeler V C, Lebel L A, Vrbanac V, Teed A, te Riele H, & MacDonald M E (2003) Mismatch repair gene Msh2 modifies the timing of early disease in Hdh(Q111) striatum. *Hum. Mol. Genet.* 12:273-281.
55. Gomes-Pereira M, Fortune M T, Ingram L, McAbney J P, & Monckton DG (2004) Pms2 is a genetic enhancer of trinucleotide CAG.CTG repeat somatic mosaicism: implications for the mechanism of triplet repeat expansion. *Hum. Mol. Genet.* 13:1815-1825.
56. Edelmann W, Umar A, Yang K, Heyer J, Kucherlapati M, Lia M, Kneitz B, Avdievich E, Fan K, Wong E, Crouse G, Kunkel T, Lipkin M, Kolodner R D, & Kucherlapati R (2000) The DNA mismatch repair genes Msh3 and Msh6 cooperate in intestinal tumor suppression. *Cancer Res.* 60:803-807.
57. Wright D J, King K, & Modrich P (1989) The negative charge of Glu-111 is required to activate the cleavage center of EcoRI endonuclease. *J. Biol. Chem.* 264:11816-11821.
58. Griffin B A, Adams S R, & Tsien R Y (1998) Specific covalent labeling of recombinant protein molecules inside live cells. *Science* 281:269-272.
59. Martin B R, Giepmans B N, Adams S R, & Tsien R Y (2005) Mammalian cell-based optimization of the biarsenical-binding tetracysteine motif for improved fluorescence and affinity. *Nature biotechnology* 23:1308-1314.

We claim:

1. A method for testing an agent for the ability to inhibit MutSβ, comprising:
   forming a first assay comprising the agent, MutLα, and MutSβ;
   evaluating interaction between MutLα and MutSβ in the first assay;
   forming a second assay comprising the agent, MutLα, and MutSα;
   evaluating interaction between MutLα and MutSα in the second assay;
   identifying the agent as an inhibitor of MutSβ-MutLα interaction and/or MutSα-MutLα interaction;
   further testing the agent for the ability to inhibit MutSβ activated MutLα endonuclease activity in a third assay; wherein the agent is a MutSβ inhibitor if MutLα endonuclease activity is inhibited compared to a control;
   wherein the assays further comprise a suitable heteroduplex DNA substrate or a control homoduplex DNA substrate and ATP.

2. The method of claim 1, wherein the heteroduplex DNA substrate comprises a suitable MutSα- or MutSβ-recognizable mismatch.

3. The method of claim 2, wherein the DNA substrate is attached to a solid support.

4. The method of claim 1 or 2, wherein interaction between MutLα and MutSβ is evaluated by detecting a DNA-MutSβ-MutLα complex.

5. The method of claim 1, wherein interaction between MutLα and MutSβ is evaluated by detecting direct binding of MutLα to MutSβ.

6. The method of claim 1, wherein interaction between MutLα and MutSβ is detected immunologically or by fluorescence resonance energy transfer.

7. The method of claim 1, wherein interaction between MutLα and MutSβ is detected chromatographically.

8. The method of claim 1, wherein the agent is a library of small molecules.

9. The method of claim 8, wherein each type of small molecule in the library is tested in separate first, second and third assays.

* * * * *